(12) United States Patent
Warner et al.

(10) Patent No.: US 7,659,833 B2
(45) Date of Patent: Feb. 9, 2010

(54) SYSTEM AND METHOD FOR REMOTELY CONTROLLING DEVICES

(76) Inventors: Thomas P. Warner, 3704 Merriweather La., Rochester Hills, MI (US) 48306-3675; Timothy DeZorzi, 1360 Windmoor Dr., South Lyon, MI (US) 48178; Howard Haselhuhn, 7182 Winding Trail, Brighton, MI (US) 48116

( * ) Notice: Subject to any disclaimer, the term of this patent is extended or adjusted under 35 U.S.C. 154(b) by 820 days.

(21) Appl. No.: 11/195,040

(22) Filed: Aug. 2, 2005

(65) Prior Publication Data
US 2007/0031782 A1   Feb. 8, 2007

(51) Int. Cl.
*G08C 19/00* (2006.01)

(52) U.S. Cl. .............. 340/825.69; 340/825.72; 340/5.64; 340/5.61; 433/101; 433/98; 606/34; 606/1

(58) Field of Classification Search .......... 340/825.69, 340/825.72, 5.6, 5.64; 606/34, 1; 433/101, 433/98
See application file for complete search history.

(56) References Cited

U.S. PATENT DOCUMENTS

| | | | |
|---|---|---|---|
| 3,742,167 A | 6/1973 | Muther | 200/86.5 |
| 3,809,454 A | 5/1974 | Brambring | 350/84 |
| 3,980,848 A | 9/1976 | Schulz et al. | 200/86.5 |
| 3,980,849 A | 9/1976 | Straihammer | 200/86.5 |
| 3,983,344 A | 9/1976 | Straihammer | 200/86.5 |
| 4,041,609 A | 8/1977 | Bresnahan et al. | 32/22 |
| 4,114,275 A | 9/1978 | Jones et al. | 32/22 |
| 4,156,187 A | 5/1979 | Murry et al. | 324/142 |
| 4,180,812 A | 12/1979 | Kaltenbach et al. | 340/706 |
| 4,354,838 A | 10/1982 | Hoyer et al. | 433/101 |
| 4,383,167 A | 5/1983 | Gmeinder et al. | 377/2 |
| 4,417,875 A | 11/1983 | Matsui | 433/101 |
| 4,523,911 A | 6/1985 | Braetsch et al. | 433/101 |
| 4,571,681 A | 2/1986 | Beier et al. | 364/413 |
| 4,798,535 A | 1/1989 | Nielsen | 433/101 |
| 4,837,857 A | 6/1989 | Scheller et al. | 455/617 |
| 4,983,901 A | 1/1991 | Lehmer | 318/685 |
| 5,223,816 A * | 6/1993 | Levinson et al. | 340/539.13 |

(Continued)

FOREIGN PATENT DOCUMENTS

WO    PCT/US2003/39870    12/2003

OTHER PUBLICATIONS

*Wireless Digital Footswitch*, Dental Products Report, Sep. 2003.

(Continued)

*Primary Examiner*—Vernal U Brown

(57) ABSTRACT

A system and a method for remotely controlling at least a first device based on operation of a foot pedal apparatus are provided. The foot pedal apparatus has a movable member. The system includes a first module configured to transmit a first RF signal in response to at least partial displacement of the moveable member of the foot pedal apparatus from a first operational position. The first signal has a first identifier. The system further includes a second module configured to receive the first RF signal and to transmit a second RF signal having the first identifier and a second identifier in response to the first RF signal. The system further includes a third module configured to receive the second RF signal and to control operation of the first device in response to the second RF signal.

14 Claims, 21 Drawing Sheets

U.S. PATENT DOCUMENTS

| | | | | |
|---|---|---|---|---|
| 5,249,121 | A | | 9/1993 | Baum et al. ............ 364/413.01 |
| 5,268,624 | A | * | 12/1993 | Zanger ...................... 318/551 |
| 5,422,521 | A | | 6/1995 | Neer et al. .................. 307/119 |
| 5,423,231 | A | | 6/1995 | Helfrich et al. ............... 74/561 |
| 5,554,894 | A | | 9/1996 | Sepielli ...................... 307/119 |
| 5,580,347 | A | | 12/1996 | Reimels ....................... 604/30 |
| 5,635,777 | A | | 6/1997 | Telymonde et al. ......... 307/119 |
| 5,712,460 | A | | 1/1998 | Carr et al. .................. 200/86.5 |
| 5,883,615 | A | | 3/1999 | Fago et al. .................. 345/156 |
| 5,931,669 | A | * | 8/1999 | Fornoff et al. ................ 433/28 |
| 5,970,457 | A | * | 10/1999 | Brant et al. ................. 704/275 |
| 6,017,354 | A | * | 1/2000 | Culp et al. .................. 606/170 |
| 6,074,388 | A | * | 6/2000 | Tockweiler et al. ........... 606/34 |
| 6,131,130 | A | * | 10/2000 | Van Ryzin ...................... 710/6 |
| 6,179,829 | B1 | * | 1/2001 | Bisch et al. ..................... 606/1 |
| 7,422,432 | B2 | * | 9/2008 | Warner ....................... 433/101 |
| 2003/0004497 | A1 | | 1/2003 | Chappius ....................... 606/1 |
| 2003/0232305 | A1 | | 12/2003 | Warner ......................... 433/98 |
| 2004/0115591 | A1 | | 6/2004 | Warner ......................... 433/98 |
| 2004/0143222 | A1 | * | 7/2004 | Spinello ...................... 604/181 |
| 2005/0130097 | A1 | | 6/2005 | Warner ....................... 433/101 |
| 2005/0130098 | A1 | | 6/2005 | Warner ....................... 433/101 |
| 2005/0251228 | A1 | * | 11/2005 | Hamel .......................... 607/60 |

OTHER PUBLICATIONS

*Wireless Wonders: Bear Foot Pedals' Foot Control*, Dental Products Report Dec. 2001.

Schleyer, Titus K.L, D.M.D, Ph.D, et al., *The Technologically Well-Equipped Dental Office*, The Journal of the American Dental Association, vol. 134, Jan. 2003, pp. 30-41.

PCT Search Report, PCT/US2003/39870, Mailing Date Mar. 28, 2005.

U.S. Patent Application For "System And Method For Remotely Controlling Devices", filed Aug. 2, 2005, U.S. Appl. No. 11/194,998.

U.S. Patent Application For "Device Selection Module And Method For Selecting Devices", filed Aug. 2, 2005, U.S. Appl. No. 11/195,044.

U.S. Patent Application For "Device Control Module And Method For Controlling Devices", filed Aug. 2, 2005, U.S. Appl. No. 11/194,997.*

* cited by examiner

SYSTEM AND METHOD FOR REMOTELY CONTROLLING DEVICES

CROSS REFERENCE TO RELATED APPLICATIONS

This application is related to the following U.S. patent applications filed contemporaneously herewith: SYSTEM AND METHOD FOR REMOTELY CONTROLLING DEVICES, Ser. No. 11/194,998; DEVICE SELECTION MODULE AND METHOD FOR SELECTING DEVICES, Ser. No. 11/194,044; DEVICE CONTROL MODULE AND METHOD FOR CONTROLLING DEVICES, Ser. No. 11/194,997, the contents of which are each incorporated herein by reference thereto.

TECHNICAL FIELD

This application relates to a system and a method for remotely controlling devices.

BACKGROUND

U.S. Pat. No. 4,156,187 discloses a remote control system for controlling devices. The system utilizes a first foot-actuated transmitter that transmits signals having one of three frequencies at a time that is received by a receiver for controlling one of three devices. A disadvantage with this system, however, is that when a second foot-actuated transmitter in another room transmits a signal having one of the three frequencies, the second foot-actuated transmitter could interfere with operation of the device. Further, the second foot-actuated transmitter could inadvertently control operation of the device when no operator is present in the room having the device.

The inventors herein have recognized a need for a system for controlling devices using first, second, and third wireless radio-frequency (RF) modules, where the third wireless RF module only responds to an RF signal having first and second identifiers associated with the first and second modules, respectively, for controlling the devices. As a result, inadvertent activation of the devices by extraneous RF signals is prevented.

SUMMARY

A system for remotely controlling at least a first device based on operation of a foot pedal apparatus in accordance with an exemplary embodiment is provided. The foot pedal apparatus has a movable member. The system includes a first module configured to transmit a first RF signal in response to at least partial displacement of the moveable member of the foot pedal apparatus from a first operational position. The first signal has a first identifier. The system further includes a second module configured to receive the first RF signal and to transmit a second RF signal having the first identifier and a second identifier in response to the first RF signal. The system further includes a third module configured to receive the second RF signal and to control operation of the first device in response to the second RF signal.

A method for remotely controlling at least a first device based on operation of a foot pedal apparatus having a movable member in accordance with another exemplary embodiment is provided. The method includes transmitting a first RF signal from a first module in response to at least partial displacement of the moveable member of the foot pedal apparatus from a first operational position. The first signal has a first identifier. The method further includes transmitting a second RF signal from a second module having the first identifier and a second identifier in response to the first RF signal. The method further includes controlling operation of the first device in response to the second RF signal.

DETAILED DESCRIPTION OF EXEMPLARY EMBODIMENTS

Figure 1:
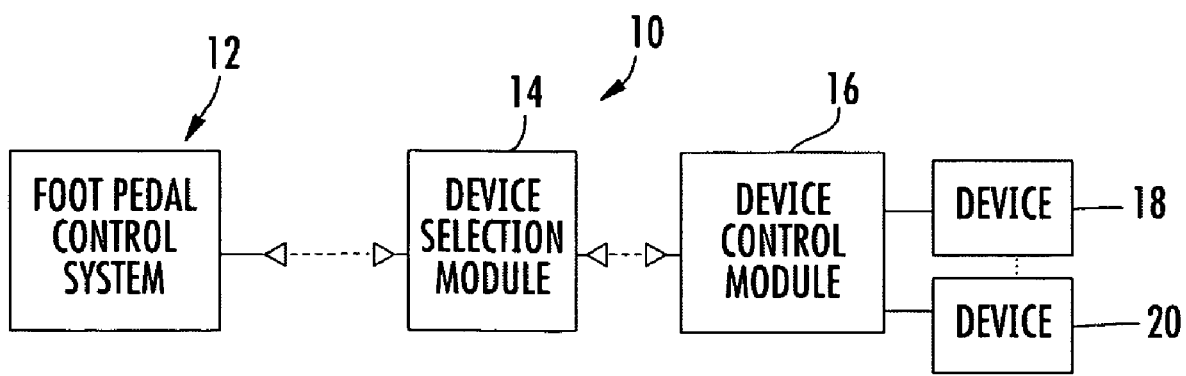
FIG. 1 is a schematic of a system for remotely controlling devices including a foot pedal control system having a foot pedal apparatus, a device selection module, and a device control module.

Referring now to the Figures, like reference numerals are used to identify identical components in the various views. Referring to FIG. 1, a system 10 for remotely controlling devices 18 and 20 is illustrated. It should be noted that in an alternate embodiment, more than two devices can be controlled by the system 10. The system 10 includes a foot pedal control system 12, a device selection module (DSM) 14, and a device control module (DCM) 16.

Figure 2:
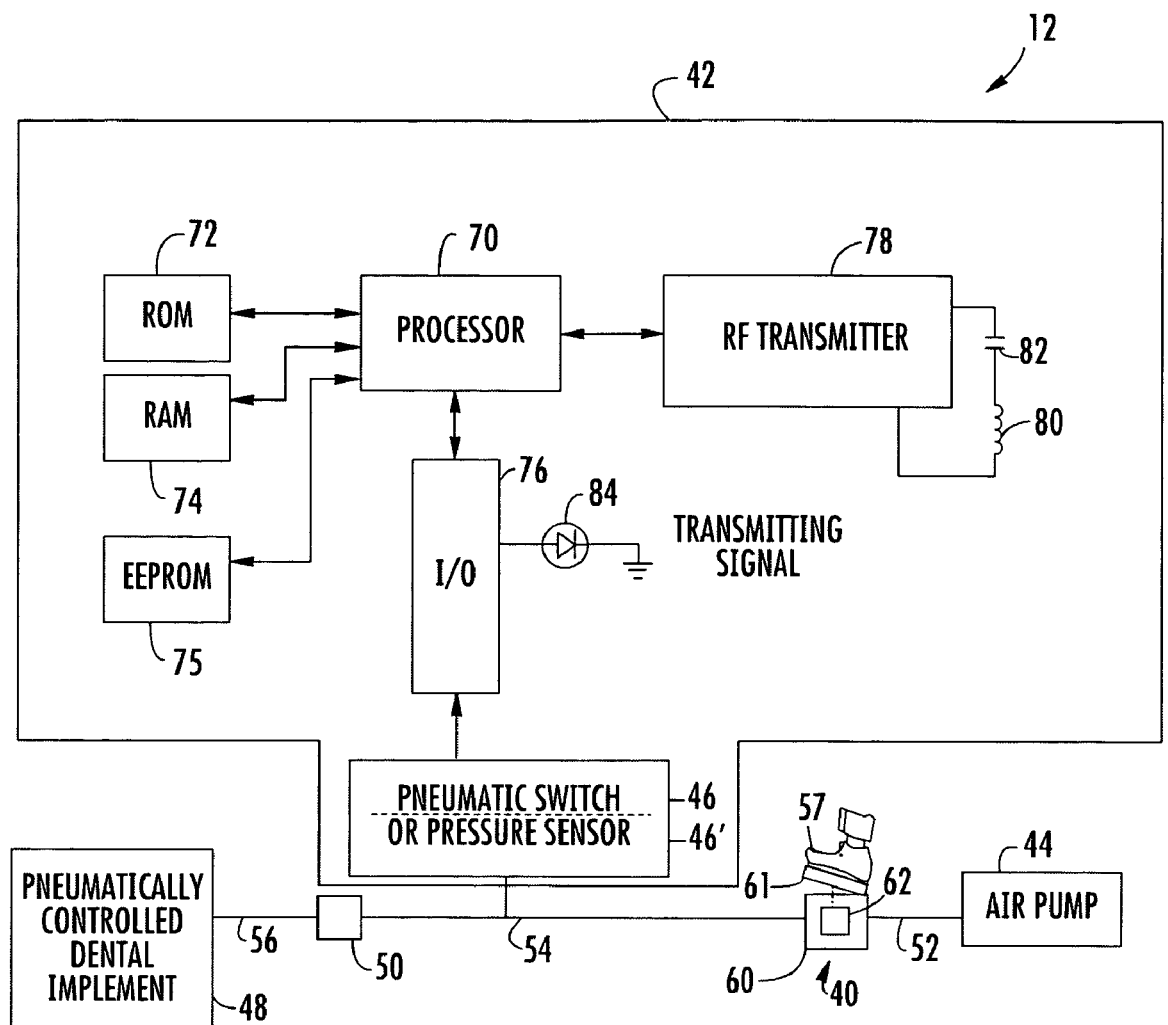
FIG. 2 is a detailed schematic of the foot pedal control system and the foot pedal monitoring module of FIG. 1.

Referring to FIG. 2, the foot pedal control system 12 is provided to monitor an operational position of a moveable member 61 of the foot pedal apparatus 62 and to transmit RF signals in response to displacement of a movable member 61 from a first operational position. The foot pedal control system 12 includes the foot pedal apparatus 40, a foot pedal monitoring module (FPMM) 42, an air pump 44, a pneumatic switch 46 or pressure sensor 46', a pneumatically controlled dental implement 48, a valve 50, and conduits 52, 54, 56.

The foot pedal apparatus 40 is provided to allow a user to displace the movable member 61 for controlling devices. The foot pedal apparatus 40 includes a housing 60, the movable member 61, and a pneumatic valve 62. The foot pedal apparatus 40 is connected to an air pump 44 via the conduit 52. The air pump 44 supplies pressurized air at a predetermined pressure through conduit 52 to the pneumatic valve 62 in the foot pedal apparatus 40. The pneumatic valve 62 is further operatively coupled to the conduit 54. The conduit 54 extends from the pneumatic valve 62 to the pneumatic valve 50. The valve 50 is further coupled to a pneumatically controlled dental implement 48. Further, a pneumatic switch 46 or a pressure sensor 46' is operatively coupled to the conduit 54. The switch 46 or pressure sensor 46' transmits a signal to I/O interface 76 that is received by the processor 70.

When a foot 57 of a user displaces the movable member 61, the pneumatic valve 62 opens to propagate pressurized air from air pump 44 to the pneumatic valve 50 for driving dental implement 48. The valve 50 only opens when a user removes dental implement 48 from a holding fixture (not shown). The inventors herein have recognized that foot pedal apparatus 40 can be further utilized to remotely control a plurality of other devices. When at least partial displacement of movable member 61 from a first operational position to a second operational position, opens or partially opens pneumatic valve 62, the pneumatic switch 46 detects an air pressure level greater than or equal to a threshold pressure level and generates a signal that is received by the I/O interface 76. In response to the signal from the switch 46, the processor 70 generates a control signal to induce the RF transmitter 78 to generate one or more RF signals as will be explained in greater detail below. Alternately, when the pressure sensor 46' is utilized instead of the pneumatic switch 46, the pressure sensor 46' generates a pressure signal indicative of the pressure in the conduit 54. When the pressure signal indicates an air pressure level greater than or equal to the threshold pressure level, the processor 70 generates a control signal to induce the RF transmitter 78 to generate one or more RF signals. It should be noted that the air pressure level in the conduit 54 is greater than or equal to the threshold pressure level when the movable member 61 at least partially opens the valve 62.

Figure 3:
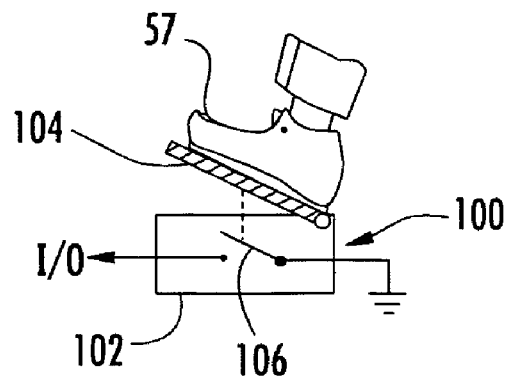
FIGS. 3 and 4 are schematics of an alternate foot pedal apparatus that can be utilized with the foot pedal control system of FIG. 1.
Figure 4:
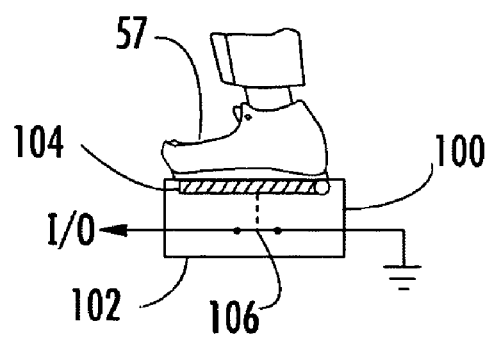

Referring to FIGS. 3 and 4, in an alternate embodiment of the foot pedal control system 12, the foot pedal apparatus 40 can be replaced with a foot pedal apparatus 100. The foot pedal apparatus 100 includes a housing 102, a movable member 104, and an electrical switch 106. The movable member 104 is operably coupled to the electrical switch 106. When the user's foot 57 pivots the movable member 104 from a first operational position (shown in FIG. 3) to a second operational position (shown in FIG. 4), the switch 106 is moved from an open operational position to a closed operational position, respectively. Thereafter, a port on the I/O interface 76 detects a ground voltage signal on the respective port that is received by the processor 70. In response to the ground voltage signal, the processor 70 is configured to generate a control signal for inducing the RF transmitter 78 to transmit one or more RF signals.

Figure 5:
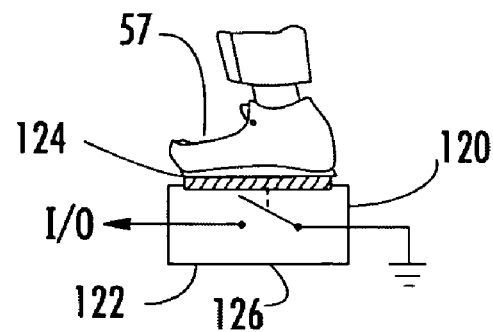
FIGS. 5 and 6 are schematics of another alternate foot pedal apparatus that can be utilized with a foot pedal control system of FIG. 1.
Figure 6:
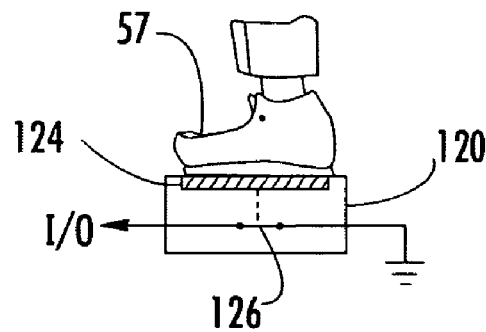

Referring to FIGS. 5 and 6, in an alternate embodiment of the foot pedal control system 12, the foot pedal apparatus 40 can be replaced with a foot pedal apparatus 120. The foot pedal apparatus 120 includes a housing 122, a movable member 124, and an electrical switch 126. The movable member 124 is operably coupled to the electrical switch 126. When the user's foot 57 displaces the movable member 124 downwardly from a first operational position (shown in FIG. 5) to a second operational position (shown in FIG. 6), the switch 126 is moved from an open operational position to a closed operational position, respectively. Thereafter, a port on the I/O interface 76 to detects a ground voltage signal on the respective port that is received by the processor 70. In response to the ground voltage signal, the processor 70 is configured to generate a control signal for inducing the RF transmitter 78 to transmit one or more RF signals.

In another alternate embodiment, the foot pedal apparatus 40 can be replaced with a foot pedal apparatus having a moveable member operably coupled to a potentiometer. The potentiometer would output a voltage signal having an amplitude proportional to an amount of displacement of the moveable member from a first operational position. The voltage signal would be received by the I/O interface 76.

Referring to FIG. 2, the foot pedal monitoring module (FPMM) 42 is provided to monitor an operational position of the movable member 61 of the foot pedal apparatus 40. Further, the FPMM 42 is provided to transmit one or more RF signals when the user displaces the movable member 61 from a first operational position. For example, the module 42 can transmit the RF signal when the user displaces the movable member 61 from the first operational position (shown in FIG. 2) to a second operational position (shown in FIG. 1). An advantage of FPMM 42 is that all of the communication between FPMM 42 and the other modules in system 10 devices are "wireless" communications thus eliminating a plurality of communication wires from the FPMM 42 to the plurality of devices being controlled. The FPMM 42 includes a processor 70, a read-only memory (ROM) 72, a random access memory (RAM) 74, an EEPROM 75, an input/output (I/O) interface 76, the RF transmitter 78, an antenna coil 80, a capacitor 82, an LED 84, the pneumatic switch 46 or the pressure sensor 46'.

The processor 70 is provided to monitor signals from either the pneumatic switch 46 or the pressure sensor 46' to determine when to generate control signals for inducing the RF transmitter 78 to generate one or more RF signals. Further, the processor 70 is configured to generate a control signal that is transmitted through the I/O interface 76 to the LED 84 for inducing the LED 84 to a emit light when the RF transmitter 78 is transmitting an RF signal. The processor 70 is operably coupled to the I/O interface 76, the RF transmitter 78, and to computer readable media including the ROM 72, the RAM 74, the EEPROM 75. It should be noted that the computer readable media utilized by the processor 70 may be implemented using any of a number of known memory devices such as PROMs, EPROMs, EEPROMs, flash memory or any other electric, magnetic, optical or combination memory device capable of storing information, some of which represent executable instructions. The ROM 72 and the RAM 74 are provided to store software algorithms and associated information utilized by the processor 70. The EEPROM 75 stores a unique FPMM identifier associated with the FPMM 12. The processor 70 comprises any device that is capable of performing an arithmetic or logical operation. For example, the processor 70 can comprise a microprocessor or a field programmable gate array, or the like. The processor 70 is operably coupled to a battery (not shown) or other external power source for supplying an operational voltage to the processor 70.

The RF transmitter 78 is provided to transmit RF signals via antenna coil 80 in response to control signals received from the processor 70. The RF transmitter 78 is operably coupled to a series combination of the capacitor 82 and the antenna coil 80. In one embodiment, the RF transmitter 78 transmits RF signals an low frequency (LF) frequency range (e.g., 30 Khz-300 Khz). In alternate embodiments, the RF transmitter 78 can transmit RF signals in one or more other frequency ranges, including for example, (i) a very low frequency (VLF) range (e.g., 9 Khz-30 Khz), (ii) a medium frequency (MF) range (e.g., 300 Khz-3 Mhz), (iii) a high frequency (HF) range (e.g., 3 Mhz-30 Mhz), (iv) an ultra high frequency (UHF) range (e.g., 300 Mhz-3 Ghz), (v) a super high frequency (SHF) range (e.g., 3 Ghz-30 Ghz), and (vi) an extremely high frequency (EHF) range (e.g., 30 Ghz-300 Ghz). Further, in one embodiment, the RF transmitter 78 can modulate each RF signal containing a transmission packet using a frequency shift keying (FSK) modulation technique. In an alternate embodiment, the RF transmitter 78 can modulate each RF signal containing a transmission packet using any other known modulation technique, such as amplitude modulation (AM), frequency modulation (FM), and amplitude shift keying (ASK), or the like. Further, the RF transmitter 78 can transmit pulsed RF signals for predetermined time intervals, such as 15 milliseconds for example.

Figure 9:
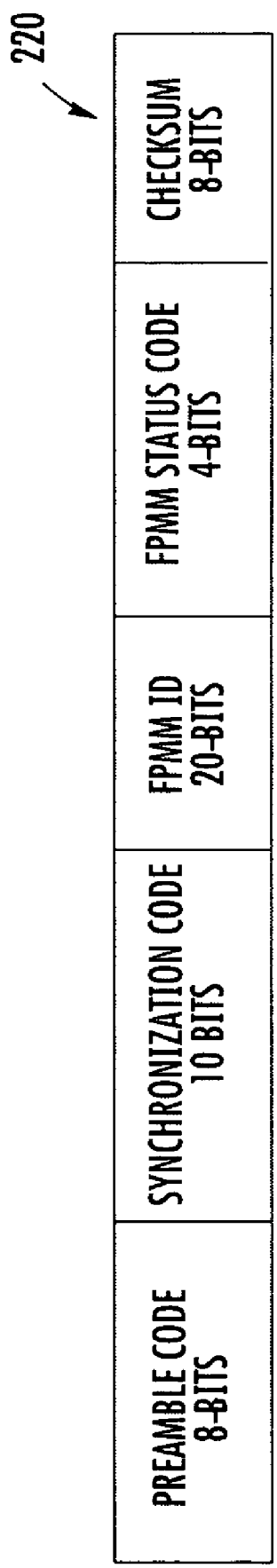
FIG. 9 is a schematic of a transmission packet in an RF signal generated by the foot pedal monitoring module of FIG. 2.

Referring to FIG. 9, a transmission packet 220 in each RF signal transmitted from the RF transmitter 78 is illustrated. The transmission packet 220 includes: (i) a preamble code, (ii) a synchronization code, (iii) a FPMM identifier (ID), a FPMM status code, and a checksum. The preamble code is utilized to wake-up and stabilize an RF receiver 139 on the DSM 14. In one embodiment, the preamble code comprises a 4-bit value. The synchronization code is utilized to allow an RF receiver to synchronize with the RF transmitter 78 for decoding a transmission packet in a received RF signal. In one embodiment, the synchronization code comprises a 10-bit value. The FPMM ID is utilized to identify a transmission packet associated with the FPMM 42. In one embodiment, the FPMM ID comprises a 20-bit value. The FPMM status code is utilized to indicate whether the movable member 61 is displaced from a first operational position. When the movable member 61 is displaced from the first operational position, the FPMM status code has a "0001" binary value (e.g., an activation command) indicating an "on" condition. Alternately, when the movable member 61 is not displaced from the first operational position, the FPMM status code has a "0000" binary value (e.g., a de-activation command) indicating an "off" condition. In one embodiment, the FPMM status code comprises a 4-bit value. The checksum value is calculated based upon the FPMM ID, and the FPMM status code, using a checksum algorithm known to those skilled in the art. It should be noted that the processor 70 stores the transmission packet 220 in a computer readable medium prior to transmission of the transmission packet 220 in an RF signal.

An advantage of the foot pedal control system 12 is that the foot pedal apparatus 40 has a single movable member utilized to selectively control a plurality of devices. Thus, other foot pedal units having a plurality of movable members or pedals for controlling a plurality of devices are no longer needed. Thus, with the foot pedal control system 12, dental or medical professionals will not have to "search" for the correct pedal from a plurality of pedals with their feet to actuate a desired device, as done with other foot pedal units having a plurality of foot pedals. Further, a plurality of other foot pedal units each having a pedal for controlling a distinct device will no longer be needed. Thus, because the foot pedal apparatus 40 can replace a plurality of other foot pedal units, a treatment room will have a less cluttered floor. Further, dental or medical professionals using the foot pedal apparatus 40 can obtain a consistent "feel" or depression force for controlling multiple devices.

Figure 7:
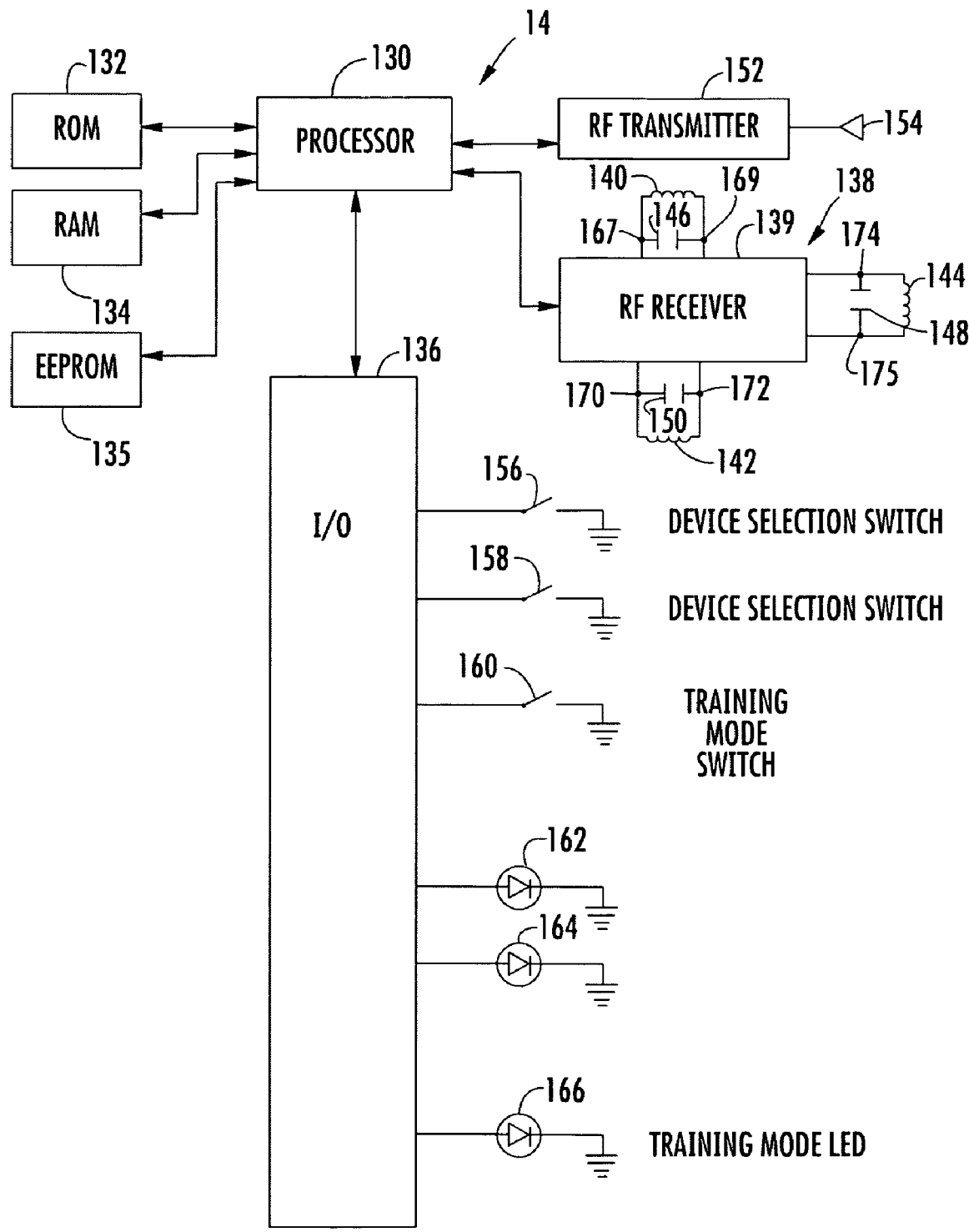
FIG. 7 is a schematic of the device selection module utilized in the system of FIG. 1.

Referring to FIG. 7, the DSM 14 is provided to receive one or more RF signals from the FPMM 42, and to transmit one or more RF signals each having a transmission packet to the DCM 16, for controlling devices operably coupled to the DCM 16. The DSM 14 is further provided to allow a user to select one of a plurality of the switches that will be associated with a respective device operably coupled to the DCM 16. The DSM 14 includes a processor 130, a ROM 132, a RAM 134, an EEPROM 135, an I/O interface 136, an RF receiver 138, antenna coils 140, 142, 144, capacitors 146, 148, 150, an RF transmitter 152, an antenna 154, switches 156, 158, 160, and LEDs 162, 164, 166.

It should be noted that the DSM 14 can be utilized with a plurality of FPMMs. Thus, a user can utilize the DSM 14 in multiple treatment rooms wherein each room has a separate FPMM, because the RF signals transmitted from DSM 14 contain both a FPMM ID from a FPMM in a specific room and a DSM ID associated with the DSM 14. Thus, the DSM can act as a master controller by only activating the DCM that is trained for an associated pair of IDs (i.e., a specific FPMM ID and DSM ID).

The DSM 14 has a training operational mode and a non-training operational mode. When the DSM 14 enters the training operational mode and subsequently receives an RF signal from the module 12, the module 14 transmits an RF signal having a training transmission packet to the DCM 16 such that the DCM 16 can store a FPMM ID and a DSM ID associated with the FPMM 42 and the DSM 14, respectively. The DCM 16 will utilize the stored FPMM ID and the DSM ID to recognize transmission packets from the DSM 14 for controlling specific devices coupled to the DCM 16. When the DSM 14 enters the non-training operational mode and subsequently receives an RF signal from the module 12, the module 14 transmits an RF signal having control information for controlling operation of the DCM 16 and a device operably coupled to the DCM 16.

The processor 130 is operably coupled to the I/O interface 136, the RF transmitter 152, the RF receiver 138, and to the computer readable media including the ROM 132, the RAM 134, and the EEPROM 135. It should be noted that the computer readable media utilized by the processor 130 may be implemented using any of a number of known memory devices such as PROMs, EPROMs, EEPROMs, flash memory or any other electric, magnetic, optical or combination memory device capable of storing information, some of which represent executable instructions. The EEPROM 135 stores a DSM ID associated with the DSM 14. The processor 130 monitors an operational state (e.g., a closed operational state or an open operational state) of the switches 156, 158, 160 utilizing the I/O interface 136. Further, the processor 130 controls the LEDs 162, 164, 166 utilizing the I/O interface 136. The processor 130 is provided to decode transmission packets in RF signals received by the RF receiver 138 from the FPMM 42. Further, the processor 130 is provided to generate transmission packets and control signals for inducing the RF transmitter 152 to transmit RF signals including transmission packets to the DCM 16 for controlling operation of the DCM 16. Further, the processor 130 is configured to enter the training operational mode when the training mode switch 160 is moved to a closed operational position for transmitting RF signals having training information to the DCM 16 such that the DCM 16 can recognize subsequent RF signals from the DSM 14. Further, the processor 130 is configured to enter a non-training operational mode when the training mode switch 160 is moved to an open operational position for transmitting RF signals having control information for controlling operation of the DCM 16. Further, the processor 130 is configured to determine when the switch 156 is moved to a closed operational position for selecting a first device operably coupled to the DCM 16. Further, the processor 130 is configured to determine when the switch 158 is moved to a closed operational position for selecting a second device operably coupled to the DCM 16. Further, the processor 130 is configured to generate a control signal for inducing the LED 162 to emit light when RF signals are being received by the RF receiver 138. Further, the processor 130 is configured to generate a control signal for inducing the LED 164 to emit light when an RF signal is being transmitted from the RF transmitter 152. Further, the processor 130 is configured to generate a control signal for inducing the LED 166 to emit light when the processor 130 enters the training operational mode. The processor 130 comprises any device that is capable of performing an arithmetic or logical operation. For example, the processor 130 can comprise a microprocessor or a field programmable gate array, or the like. The processor 130 is operably coupled to a battery (not shown) or an external power supply for supplying an operational voltage to the processor 130.

The RF transmitter 152 is provided to transmit RF signals via antenna coil 154 in response to control signals received from the processor 130. In an embodiment, the RF transmitter 152 transmits RF signals in a medium frequency (MF) range (e.g., 300 Khz-3 Mhz). In alternate embodiments, the RF transmitter 152 can transmit RF signals in one or more other frequency ranges, including for example, (i) the VLF range (e.g., 9 Khz-30 Khz), (ii) the LF range (e.g., 30 Khz-300 Khz), (iii) the HF range (e.g., 3 Mhz-30 Mhz), (iv) the UHF range (e.g., 300 Mhz-3 Ghz), (v) the SHF range (e.g., 3 Ghz-30 Ghz), and (vi) the EHF range (e.g., 30 Ghz-300 Ghz). Further, in one embodiment, the RF transmitter 152 can modulate each RF signal containing a transmission packet using a FSK modulation technique. In an alternate embodiment, the RF transmitter 152 can modulate each RF signal containing a transmission packet using any other known modulation technique, such as AM, FM, or ASK, or the like. Further, the RF transmitter 152 can transmit pulsed RF signals for predetermined time intervals, such as 15 milliseconds for example.

The RF receiver 138 is provided to receive RF signals from the FPMM 42. The RF receiver 138 includes an RF receiver microchip 139, antenna coils 140, 142, 144, and capacitors 146, 148, 150. The RF receiver microchip 139 is electrically coupled at nodes 167, 169 to a parallel combination of the capacitor 146 and the antenna coil 140. The RF receiver microchip 139 is electrically coupled at nodes 170, 172 to a parallel combination of the capacitor 150 and the antenna 142. Further, the RF receiver microchip 139 is electrically coupled at nodes 174, 175 to a parallel combination of the capacitor 148 and the antenna coil 144. The antenna coils 140, 142, 144 are positioned for receiving RF signals along at least one of three axes. In particular, a long axis of the antenna coil 140 is disposed substantially perpendicular to a long axis of the antenna coil 144. Further, a long axis of the antenna coil 144 is disposed substantially perpendicular to a long axis of the antenna coil 142.

Figure 10:
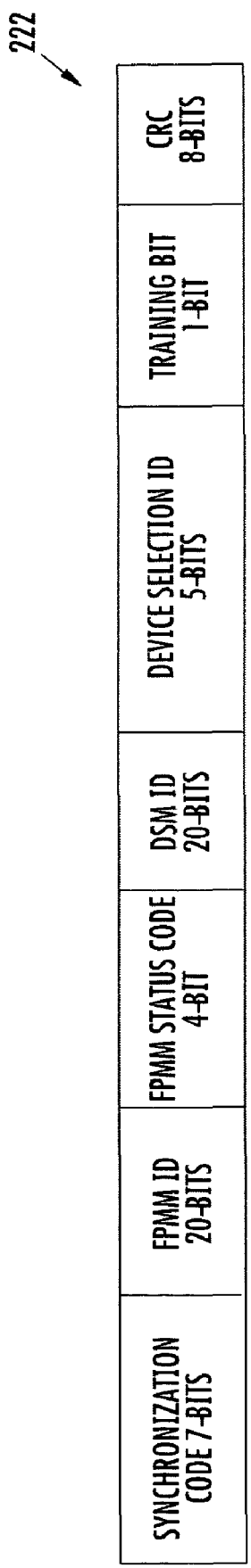
FIG. 10 is a schematic of a transmission packet in an RF signal generated by the device selection module of FIG. 7.

Referring to FIG. 10, a transmission packet 222 in each RF signal transmitted from the RF transmitter 152 is illustrated. The transmission packet 222 includes: (i) a synchronization code, (ii) an FPMM ID, (iii) a FPMM status code, (iv) a DSM ID, (v) a device selection ID, (vi) a training bit, and (vii) a CRC code. The synchronization code is utilized to allow an RF receiver in the DCM 16 to synchronize with the RF transmitter 152 for decoding a transmission packet in a received RF signal. In one embodiment, the synchronization code comprises a 7-bit value. The FPMM ID is utilized to identify a transmission packet associated with the FPMM 42. In one embodiment, the FPMM ID comprises a 20-bit value. The FPMM status code is utilized to indicate whether the movable member 61 is displaced from a first operational position. When the movable member 61 of the foot pedal apparatus 40 is displaced from the first operational position, the FPMM status code has a "0001" binary value indicating an "on" condition. Alternately, when the movable member 61 is not displaced from the first operational position, the FPMM status code has a "0000" binary value indicating an "off" condition. The DSM ID is utilized to identify a transmission packet associated with the DSM 14. In one embodiment, the DSM ID comprises a 20-bit value. The device selection ID is utilized to identify which device selection switch on the DSM 14 has been moved to a closed operational position, and also which device is to be controlled by the DCM 16. The training bit is utilized to indicate whether the transmission packet is a training transmission packet or not. When the training bit has a "1" binary value indicating the transmission packet is a training transmission packet, the DCM 16 will associate a bi-directional switch therein and a device operably coupled to the bi-directional switch to the FPMM ID, the DSM ID, and the device selection ID. When the training bit has a "0" binary value indicating a transmission packet is not a training transmission packet, the DCM 16 will control the bi-directional switch and the device operably coupled to the bi-directional switch, that are associated with the received FPMM ID, the DSM ID, and the device selection ID. The cyclic redundancy code (CRC) is calculated based upon the FPMM ID, the FPMM status code, the DSM ID, the device selection ID, and the training bit, using an algorithm known to those skilled in the art. It should be noted that the processor 130 stores the transmission packet 222 in a computer readable medium prior to transmission of the transmission packet 222 in an RF signal.

Figure 8:
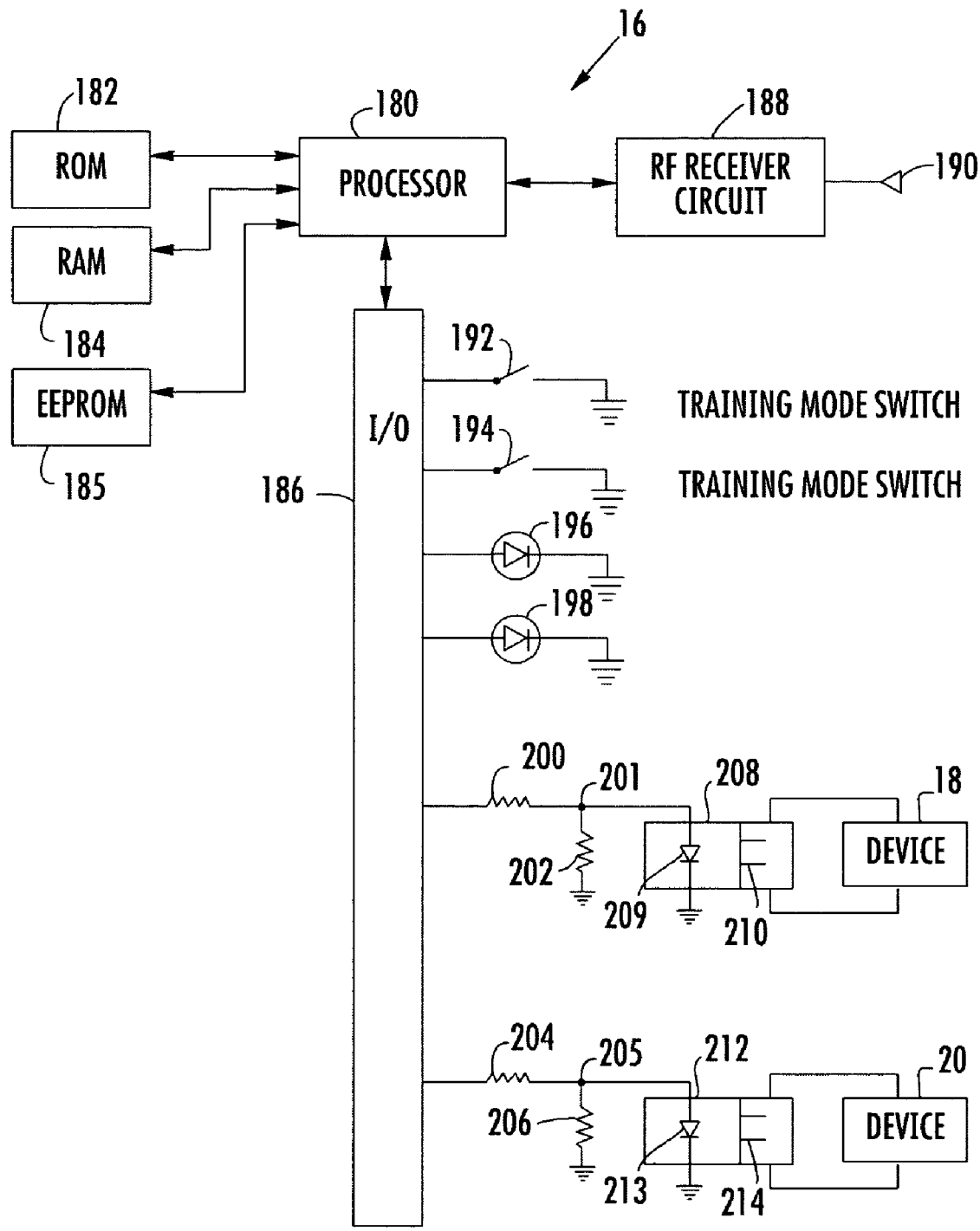
FIG. 8 is a schematic of the device control module utilized in the system of FIG. 1.

Referring to FIG. 8, the DCM is provided to receive one or more RF signals from the DSM 14 for controlling devices operably coupled to the DCM 16. The DCM 16 includes a processor 180, a ROM 182, a RAM 184, an EEPROM 185, an I/O interface 186, an RF receiver circuit 188, an antenna coil 190, switches 192, 194, LEDs 196, 198, resistors 200, 202, 204, 206, and optically coupled bi-directional switches 208, 212.

The processor 180 is provided to control operation of the bi-directional switches 208, 212 to control operation of the devices 18, 20 respectively, based on RF signals received from the DSM 14. The processor 180 is operably coupled to the RF receiver circuit 188, the I/O interface 186 and to the computer readable media including the ROM 182, the RAM 184, the EEPROM 185. It should be noted that the computer readable media utilized by the processor 180 may be implemented using any of a number of known memory devices such as PROMs, EPROMs, EEPROMs, flash memory or any other electric, magnetic, optical or combination memory device capable of storing information, some of which represent executable instructions. The processor 180 is configured to monitor an operational state (e.g., a closed operational state or an open operational state) of the switches 192, 194 utilizing the I/O interface 186, and to control the LEDs 196, 198 and the bi-directional switches 208, 212 utilizing the I/O interface 186. Further, the processor 180 is configured to decode transmission packets in RF signals received by the RF receiver circuit 188 from the DSM 14.

The processor 180 has a training operational mode and a non-training operational mode. In particular, the processor 180 is configured to enter the training operational mode when one of the training mode switches 192, 194 is moved to a closed operational position. When the training mode switch 192 is moved to the closed operational position and the RF receiver circuit 188 subsequently receives a first RF signal having a first transmission packet with a training bit equal to "1" from the DSM 14, the processor 180 stores the FPMM ID, the DSM ID, and the device selection ID from the first transmission packet in the EEPROM 185. Further, the processor 180 associates the stored values from the first transmission packet with the bi-directional switch 208 that is operably coupled to the device 18. Alternately, when the training mode switch 194 is moved to the closed operational position and the RF receiver circuit 188 subsequently receives a second RF signal having a second transmission packet with a training bit equal to "1" from the DSM 14, the processor 180 stores the FPMM ID, the DSM ID, and the device selection ID from the second transmission packet in the EEPROM 185. Further, the processor 180 associates these stored values from the second transmission packet with the bi-directional switch 208 that is operably coupled to the device 18. When the processor 180 decodes a transmission packet having a FPMM ID, a DSM ID, and a device selection ID associated with the bi-directional switch 208, the processor 180 generates a control signal for inducing the bi-directional switch 208 to activate the device 18. Further, the processor 180 generates a control signal for inducing the LED 196 to emit light. Alternately, when the processor 180 decodes a transmission packet having a FPMM ID, a DSM ID, and a device selection ID associated with the bi-directional switch 212, the processor 180 generates a control signal for inducing the bi-directional switch 212 to activate the device 20. Further, the processor 180 generates a control signal for inducing the LED 198 to emit light. The processor 180 comprises any device that is capable of performing an arithmetic or logical operation. For example, the processor 180 can comprise a microprocessor or a field programmable gate array, or the like. The processor 180 can be operably coupled to a battery (not shown) or another electric power source for supplying an operational voltage to the processor 180.

The optically coupled bi-directional switch 208 is provided to control operation of the device 18 in response to a control signal from the processor 180. In particular, the switch 208 activates the device 18 in response to a control signal received from the processor 180 via the I/O interface 186. Further, the switch 208 de-activates the device 18 when the switch 208 no longer receives the control signal from the processor 180. The switch 208 includes a light emitting element 209 and an optically responsive switching element 210. As shown, the light-emitting element 209 is electrically coupled between a node 201 and electrical ground. Further, a resistor 200 is electrically coupled between the I/O interface 186 and the node 201, and a resistor 202 is electrically coupled between the node 201 and electrical ground. Further, the device 18 is electrically coupled to the optically responsive switching element 210. In particular, when the bi-directional switch 208 receives a control signal from the processor 180, the light-emitting element 209 emits light inducing the optically responsive switching element 210 to activate the device 18. Alternately, when the bi-directional switch 208 does not receive the control signal from the processor 180, the light-emitting element 209 stops emitting light inducing the optically responsive switching element 210 to de-activate the device 18.

The optically coupled bi-directional switch 212 is provided to control operation of the device 20 in response to a control signal from the processor 180. In particular, the switch 212 activates the device 20 in response to a control signal received from the processor 180 via the I/O interface 186. Further, the switch 212 de-activates the device 20 when the switch 212 no longer receives the control signal from the processor 180. The switch 212 includes a light emitting element 213 and an optically responsive switching element 214. As shown, the light-emitting element 213 is electrically coupled between a node 205 and electrical ground. Further, a resistor 204 is electrically coupled between the I/O interface 186 and the node 205, and a resistor 206 is electrically coupled between the node 205 and electrical ground. Further, the device 20 is electrically coupled to the optically responsive switching element 214. In particular, when the bi-directional switch 212 receives a control signal from the processor 180, the light-emitting element 213 emits light inducing the optically responsive switching element 214 to activate the device 20. Alternately, when the bi-directional switch 212 does not receive the control signal from the processor 180, the light-emitting element 213 stops emitting light inducing the optically responsive switching element 212 to de-activate the device 20.

The devices 18, 20 may comprise any electrically, pneumatically, magnetically, or hydraulically actuated device. For example, devices 18, 20 may comprise electrically, pneumatically, magnetically, or hydraulically actuated medical or dental devices. Further, devices 18, 20 may comprise one or more of the following devices: a drill, a dental chair whose chair position can be adjusted automatically, an infrared photo-optic imaging camera, a dental irrigator, an intra-oral camera, a laser, an air-abrasion unit, an electro-surgery unit, an ultrasonic teeth cleaning unit, a piezo-ultrasonic unit, an air polishing prophylaxis device, a gum depth measurement probe, a surgical microscope, a microprocessor controlled anesthetic delivery system, and an endodontic heat source device.

For example, one or more of the devices 18, 20 can comprise a torque control motor drill sold under the trademark Tecnika and is manufactured by Advanced Technology Research (ATR), located at Via del Pescino, 6, 51100 Pistoia, Italy, and sold in the United States by Dentsply Tulsa Dental at 5001 E. $68^{th}$, Tulsa, Okla. 74136-3332. Further, it should be noted that the DCM 16 could be used to control operation of any electrically controlled or pneumatically controlled drill.

Further, for example, one or more of the devices 18, 20 can comprise a dental chair sold under the trademark Priority® manufactured by A-DEC located at 2601 Crestview Drive, Newberg, Oreg., which provides elevational control of the chair, tilting of the back of the chair, and memory recall positions. Thus, the elevation position, tilting position, and other variable position adjustments could be controlled by the inventive control system. Further, it should be noted that the DCM 16 could be used to control operation of any electrically controlled or hydraulically controlled dental chair or control unit associated with the dental chair.

Further, for example, one or more of the devices 18, 20 can comprise an infrared photo-optic imaging camera sold under the trademark CEREC® manufactured by Sirona Dental Systems located at Fabrikstrabe 31, 64625 Bensheim, Hessen, Germany, and sold in the United States by Patterson Dental Supply, Inc., located at 1031 Mendota Heights Rd., Saint Paul, Minn. 55120. Further, it should be noted that the DCM 16 could be used to control any imaging camera that can be automatically or externally controlled to generate a digital image or a film image.

Further, for example, one or more of the devices 18, 20 can comprise a dental irrigator sold under the trademark Piezon® Master 600, manufactured by Electro Medical Systems located at 12092 Forestgate Drive, Dallas Tex., 75243. Further, it should be noted that the DCM 16 could be used to control operation of any dental irrigator or dental irrigator control system that directs fluid under pressure therethrough.

Further, for example, one or more of the devices 18, 20 can comprise an intra-oral camera sold under the trademark Prism™, manufactured by Professional Dental Technologies, Inc., located at 2410 Harrison Street, Batesville, Ark. 72501, or the AcuCam® Concept IV manufactured by Gendex, a division of Dentsply International located at 901 W. Oakton St., Des Plains, Ill. 60018-1884. Further, it should be noted that the DCM 16 could be used to control operation of any intra-oral camera (or video capture card or video capture computer associated with the camera) to generate, store, retrieve, display, or print a digital or analog video image.

Further, for example, one or more of the devices 18, 20 can comprise a laser sold under the trademark Odyssey™, manufactured by Ivoclar Vivadent Inc., located at 175 Pineview Drive, Amherst, N.Y. 14228. Alternately, the system could be utilized with a laser sold under the trademark Waterlase®, manufactured by Biolase Technology, Inc., located at 981 Calle Amanecer, San Clemente, Calif. 92673. Further, it should be noted that the DCM 16 could be used to control operation of any other known laser.

Further, for example, one or more of the devices 18, 20 can comprise an air-abrasion unit sold under the trademark Prep-Start™, manufactured by Danville Engineering, located at 2021 Omega Road, San Ramon Calif. 94583. Further, it should be noted that the DCM 16 could be used to control operation of any other type of air-abrasion unit utilized in dental procedures, in medical procedures, or during processing or cleaning of manufactured goods.

Further, for example, one or more of the devices 18, 20 can comprise an electro-surgery unit sold under the trademark Hyfrecator® 2000, manufactured by ConMed® Corporation, located at 310 Broad Street, Utica, N.Y. 13501. Further, it should be noted that the DCM 16 could be used to control operation of any other electro-surgery unit that utilizes electrical energy for removing tissue or bone.

Further, for example, one or more of the devices 18, 20 can comprise the ultrasonic teeth cleaning unit sold under the trademark Cavitron® 3000 manufactured by Dentsply International located at 901 W. Oakton Street, Des Plains, Ill. 60018-1884. Further, it should be noted that the DCM 16 could be used to control operation of any other ultrasonic teeth cleaning unit.

Further, for example, one or more of the devices 18, 20 can comprise a piezo-ultrasonic unit sold under the trademark Spartan MTS™, manufactured by Obtura Spartan located at 1663 Fenton Business Park Court, Fenton, Mo. 63026. Further, it should be noted that the DCM 16 could be used to control operation of any other piezo-ultrasonic unit that agitates or vibrates a tip for cleaning teeth or removing tooth structure. Piezo-ultrasonic units may have fluid cooled tips.

Further, for example, one or more of the devices 18, 20 can comprise an air polishing prophylaxis device sold under the trademark Cavitron® Prophy-Jet®, manufactured by Dentsply International located at 901 W. Oakton Street, Des Plains, Ill. 60018-1884. Further, it should be noted that the DCM 16 could be used to control operation of any other air polishing prophylaxis device that uses compressed air for delivering a fluid and/or an abrasive compound out of a nozzle for cleaning teeth and gums.

Further, for example, one or more of the devices 18, 20 can comprise the gum depth measurement probe sold under the trademark Florida Probe®, manufactured by Florida Probe Corporation, located at 3700 NW 91$^{st}$ Street, Suite C-100, Gainesville, Fla. 32606. Further, it should be noted that the DCM 16 could be used to control operation of any other gum depth measurement probe that can be automatically or externally controlled to take a gum depth measurement.

Further, for example, one or more of the devices 18, 20 can comprise a surgical microscope sold under the trademark OPMI® pico, manufactured by Carl Zeiss Surgical Inc., located at One Ziess Drive, Thornwood, N.Y. 10594. Alternately, the DCM 16 could utilized with the surgical microscope sold under the trademark Protégé™, manufactured by Global Surgical Corporation, located at 3610 Tree Court Industrial Blvd., St. Louis, Mo. 63122-6622. Further, it should be noted that the DCM 16 could be used to control operation of any other surgical microscope that includes one or more of: automatically controllable height adjustment, automatically controllable focusing, automatically controllable field of view size, viewing lights, and a camera associated with the surgical microscope.

Further, for example, one or more of the devices 18, 20 can comprise an anesthetic delivery system sold under the trademark The Wand™ II, manufactured by the Dental Division of Milestone Scientific located at 151 S. Pfingsten Road, Deerfield, Ill. 60015. Further, it should be noted that the DCM 16 could be used to control operation of any other microprocessor-controlled anesthetic delivery system that delivers predetermined amounts of an anesthetic to a medical or dental patient.

Further, for example, one or more of the devices 18, 20 can comprise an endodontic heat source device sold under the trademark System B HeatSource™ model 1005, manufactured by Analytic-Sybron Dental Specialties located at 1332 South Lone Hill Avenue, Glendora, Calif. 91740. Further, it should be noted that the DCM 16 could be used to control operation of any other endodontic heat source device.

Figure 11:
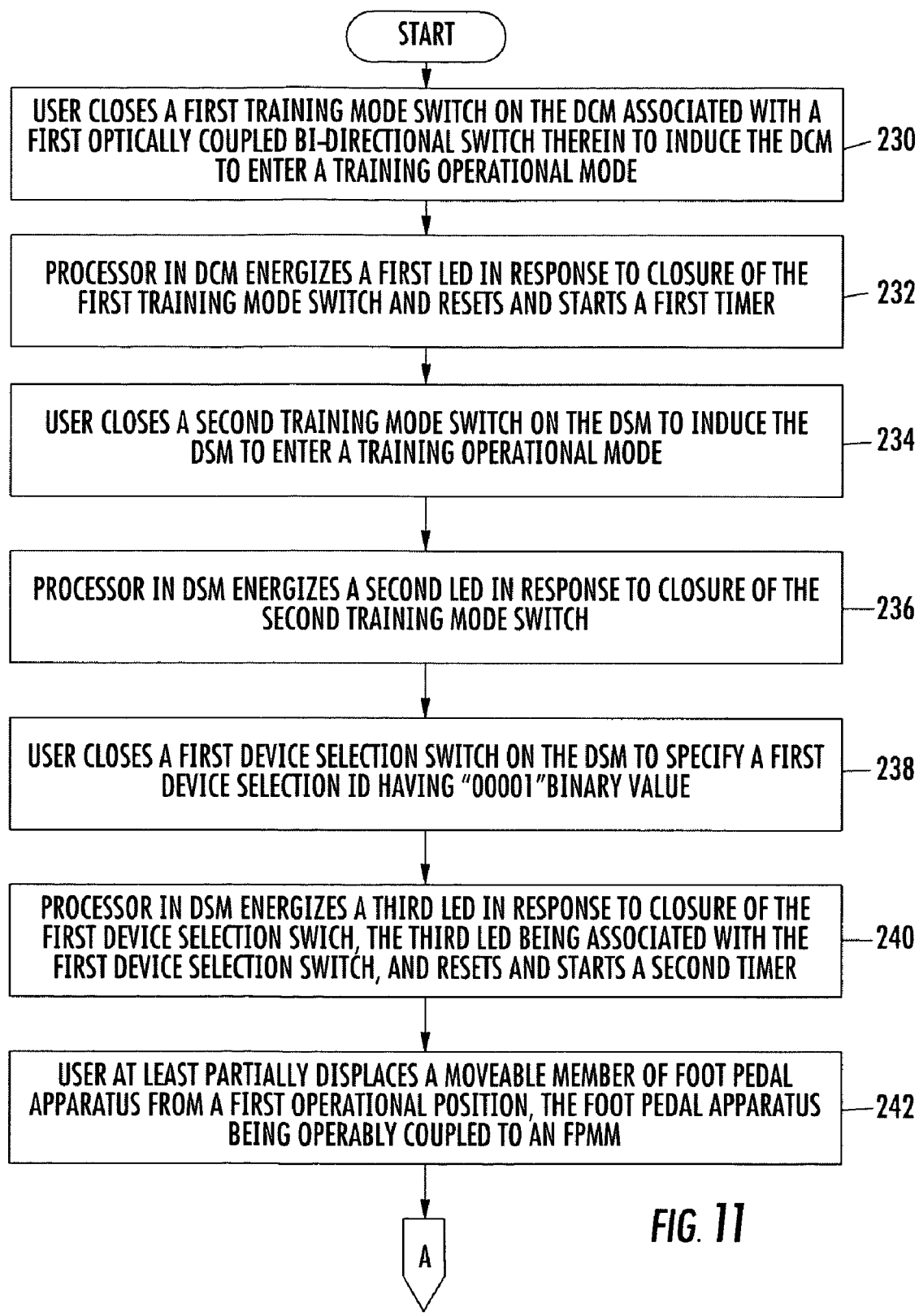
FIGS. 11-13 are flowcharts of a method for training the device control module of FIG. 8 for controlling a first device.
Figure 12:
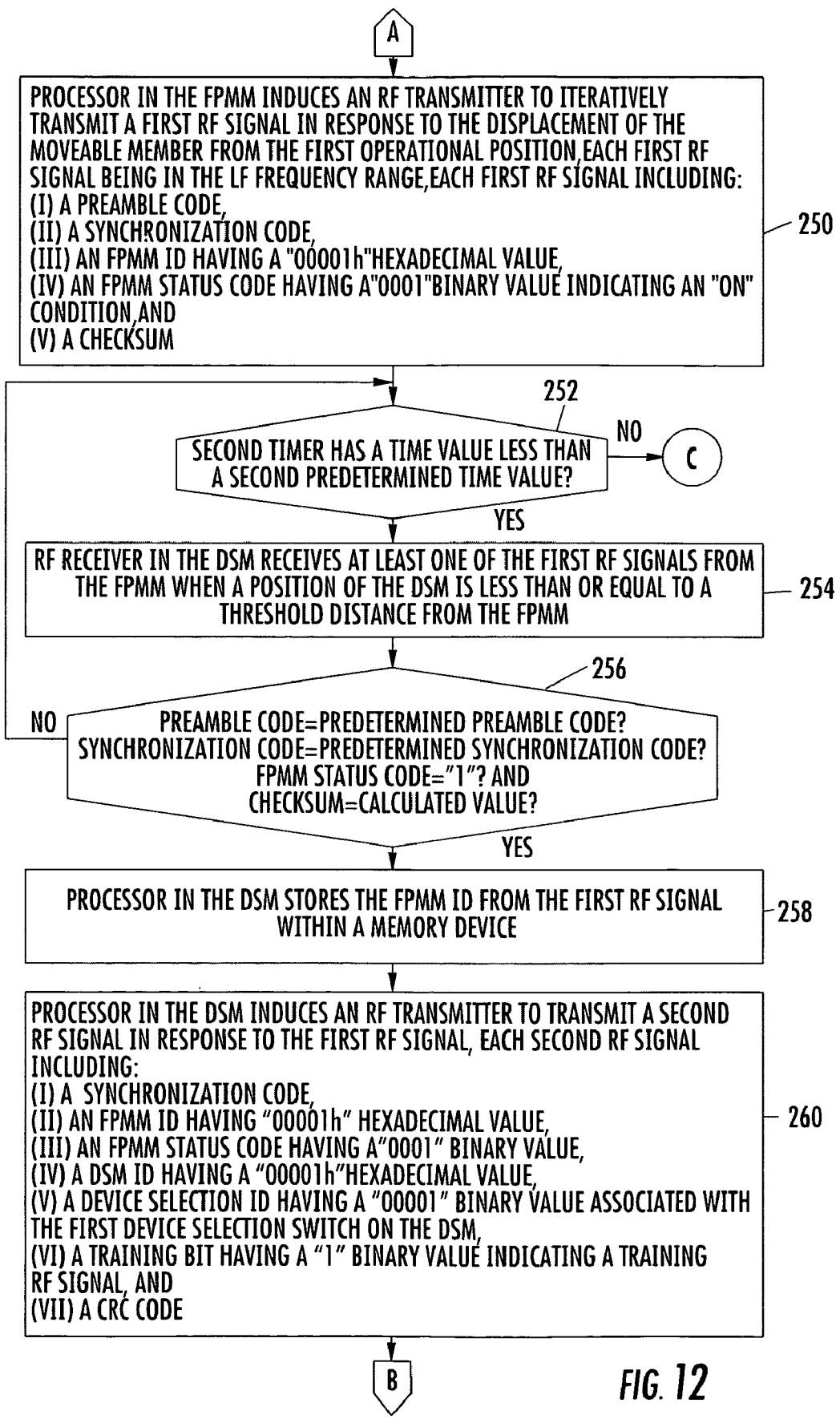
Figure 13:
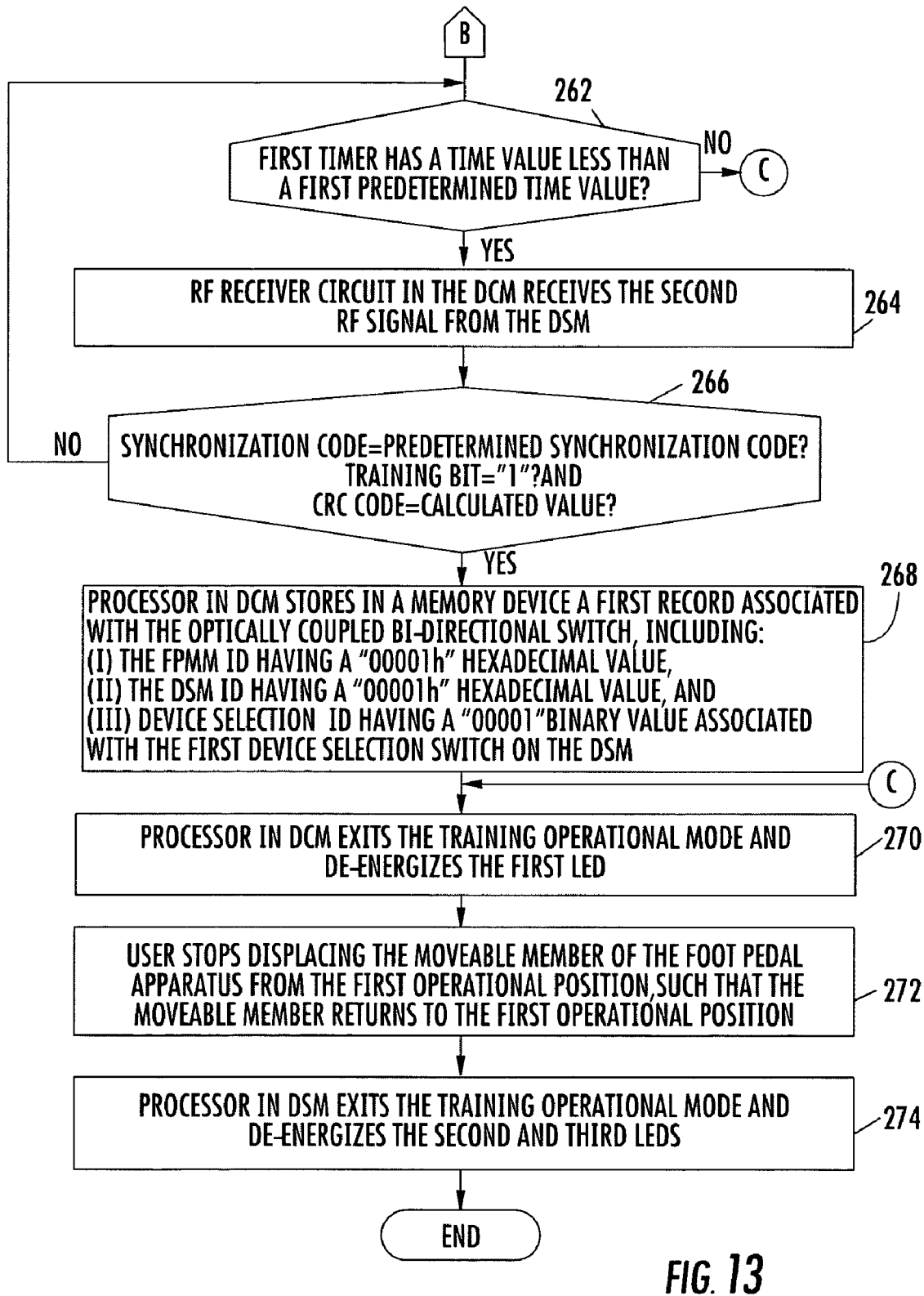

Referring to FIGS. 11-13, a method for training the DCM 16 to respond to RF signals from the DSM 14 for controlling the device 18 will now be explained. The method can be implemented utilizing the system 10 described above.

At step 230, a user closes a training mode switch 192 on the DCM 16 associated with an optically coupled bi-directional switch 208 therein to induce the DCM 16 to enter a training operational mode.

Next at step 232, the processor 180 in the DCM 16 energizes an LED 196 in response to closure of the training mode switch 192 and resets and starts a first timer.

Next at step 234, the user closes a training mode switch 160 on the DSM 14 to induce the DSM 14 to enter a training operational mode.

Next at step 236, the processor 130 in the DSM 14 energizes a LED 166 in response to closure of the training mode switch 160.

Next at step 238, the user closes a device selection switch 156 on the DSM 14 to specify a first device selection ID having a "00001" binary value.

Next at step 240, the processor 130 in the DSM 14 energizes an LED 162 in response to closure of the device selection switch 156. The LED 162 is associated with the device selection switch 156. Further, the processor 130 resets and starts a second timer.

Next at step 242, the user at least partially displaces a moveable member 61 of foot pedal apparatus 40 from a first operational position. The foot pedal apparatus 40 is operably coupled to the FPMM 42.

Next at step 250, the processor 70 in the FPMM 42 generates a control signal to induce the RF transmitter 78 to iteratively transmit a first RF signal in response to the displacement of the moveable member 61 from the first operational position. In one embodiment, each first RF signal is in the LF frequency range. Further, each first RF signal includes: (i) a preamble code, (ii) a synchronization code, (iii) an FPMM ID having a "00001h" hexadecimal value, (iv) an FPMM status code having a "0001" binary value indicating an "on" condition, and (v) a checksum.

Next at step 252, the processor 130 makes a determination as to whether the second timer has a time value less then a second predetermined time value. If the value of step 252 equals "yes", the method advances to step 254. Otherwise, the method advances to step 270.

At step 254, the RF receiver 138 in the DSM 14 receives at least one of the first RF signals from the FPMM 42 when a position of the DSM 14 is less than or equal to a threshold distance from the FPMM 42. In one embodiment, the threshold distance is less than or equal to ten feet. Of course, in alternate embodiments, the threshold distance could be greater than ten feet.

Next at step 256, the processor 130 makes a determination as to whether the following conditions are present with respect to the first RF signal: (i) preamble code=predetermined preamble code, (ii) synchronization code=predetermined synchronization code, (iii) FPMM status code="1", and (iv) checksum=calculated value. In this step, the calculated value corresponds to a calculated checksum value calculated by the processor 130 based on at least a portion of the transmission packet in the first RF signal. If the value of step 256 equals "yes", indicating the foregoing conditions are present, the method advances to step 258. Otherwise, the method returns to step 252.

At step 258, the processor 130 in the DSM 14 stores the FPMM ID from the first RF signal within the EEPROM 135.

Next at step 260, the processor 130 in the DSM 14 generates a control signal to induce the RF transmitter 152 to transmit a second RF signal in response to the first RF signal. Each second RF signal includes: (i) a synchronization code, (ii) an FPMM ID having "00001h" hexadecimal value, (iii) an FPMM status code having a "0001" binary value, (iv) a DSM ID having a "00001h" hexadecimal value, (v) a device selection ID having a "00001" binary value associated with the device selection switch 156 on the DSM 14, (vi) a training bit having a "1" binary value indicating a training RF signal, and (vii) a CRC code.

Next at step 262, the processor 180 in the DCM 16 makes a determination as to whether the first timer has a time value less than a first predetermined time value. If the value of step 262 equals "yes", the method advances to step 264. Otherwise, the method advances to step 270.

At step 264, the RF receiver circuit 188 in the DCM 16 receives the second RF signal from the DSM 14.

Next at step 266, the processor 180 makes a determination as to whether the following conditions are present with respect to the second RF signal: (i) synchronization code=predetermined synchronization code, (ii) training bit="1", and (iii) CRC code=calculated value. If the value of step 266 equals "yes", indicating the foregoing conditions are present, the method advances to step 268. Otherwise, the method returns to step 262.

Next at step 268, the processor 180 in the DCM 16 stores in the EEPROM 185 a first record associated with the first optically coupled bi-directional switch, including: (i) the FPMM ID having a "00001h" hexadecimal value, (ii) the DSM ID having a "00001h" hexadecimal value, and (iii) device selection ID having a "00001" binary value associated with the device selection switch 156 on the DSM 14.

At step 270, the processor 180 in the DCM 16 exits the training operational mode and de-energizes the LED 196.

Next at step 272, the user stops displacing the moveable member 61 of the foot pedal apparatus 40 from the first operational position, such that the moveable member 61 returns to the first operational position.

Next at step 274, the processor 130 in the DSM 14 exits the training operational mode and de-energizes the LEDs 162, 166. After step 274, the method is exited.

Figure 14:
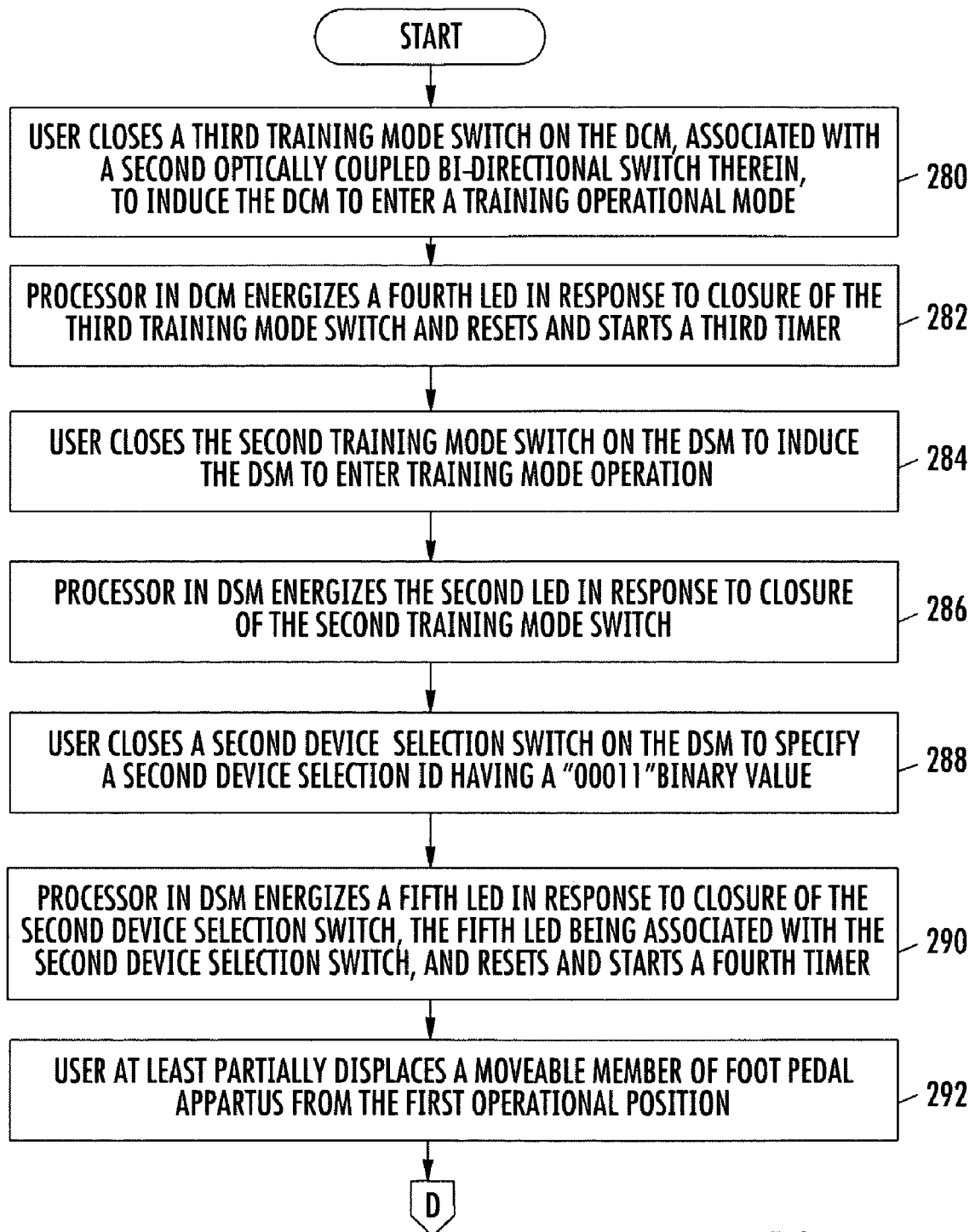
FIGS. 14-16 are flowcharts of a method for training the device control module of FIG. 8 for controlling a second device.
Figure 15:
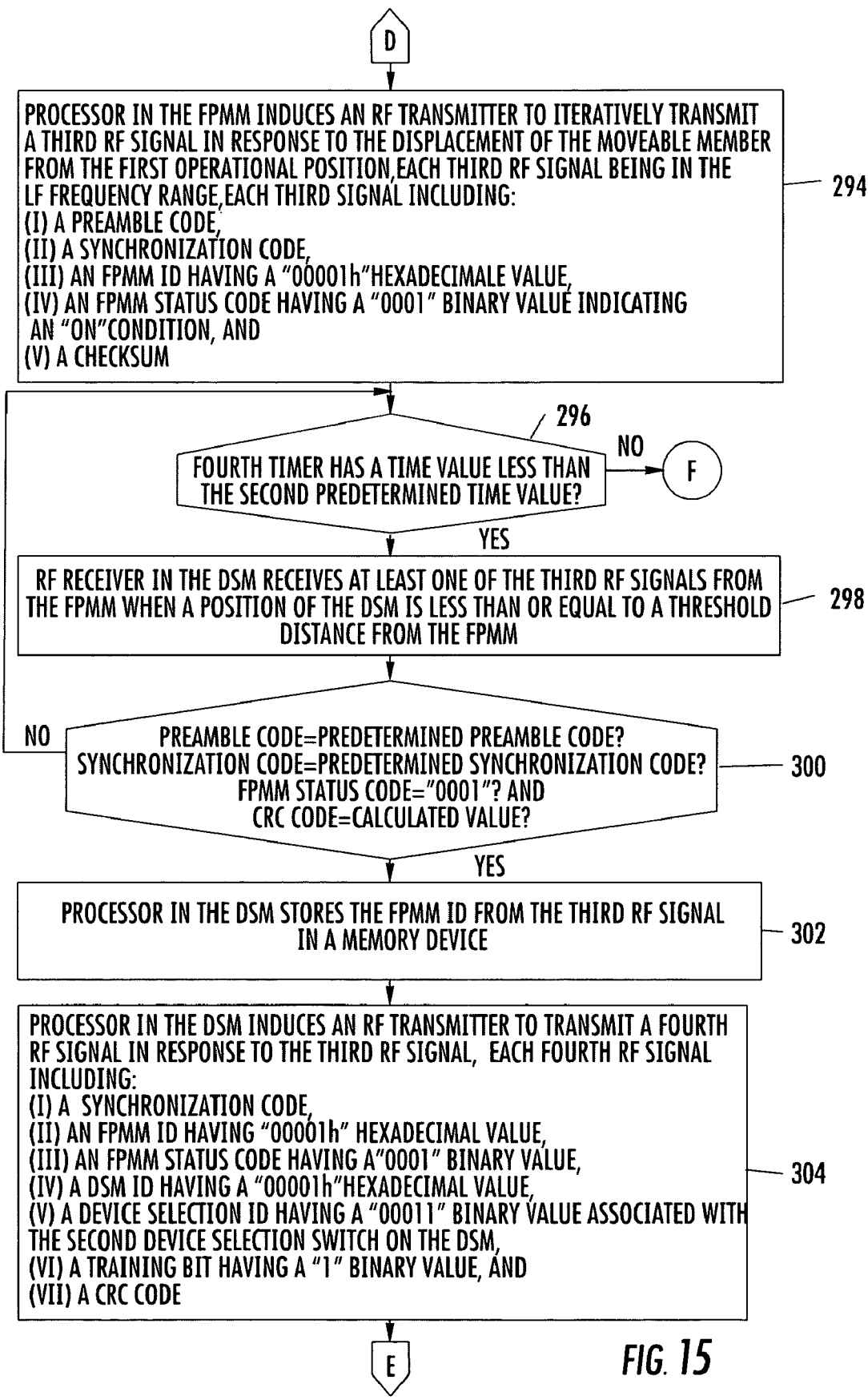
Figure 16:
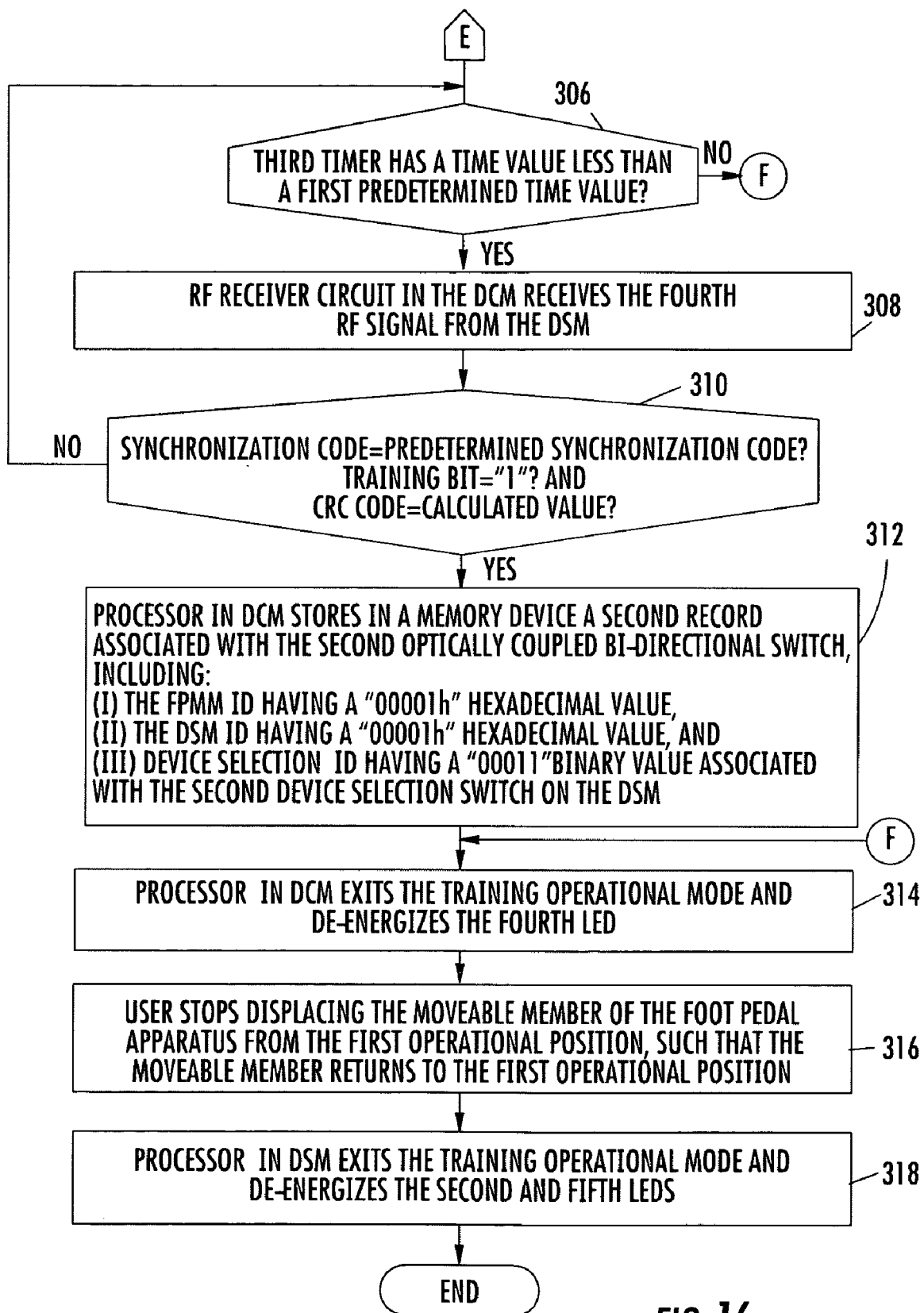
Figure 17:
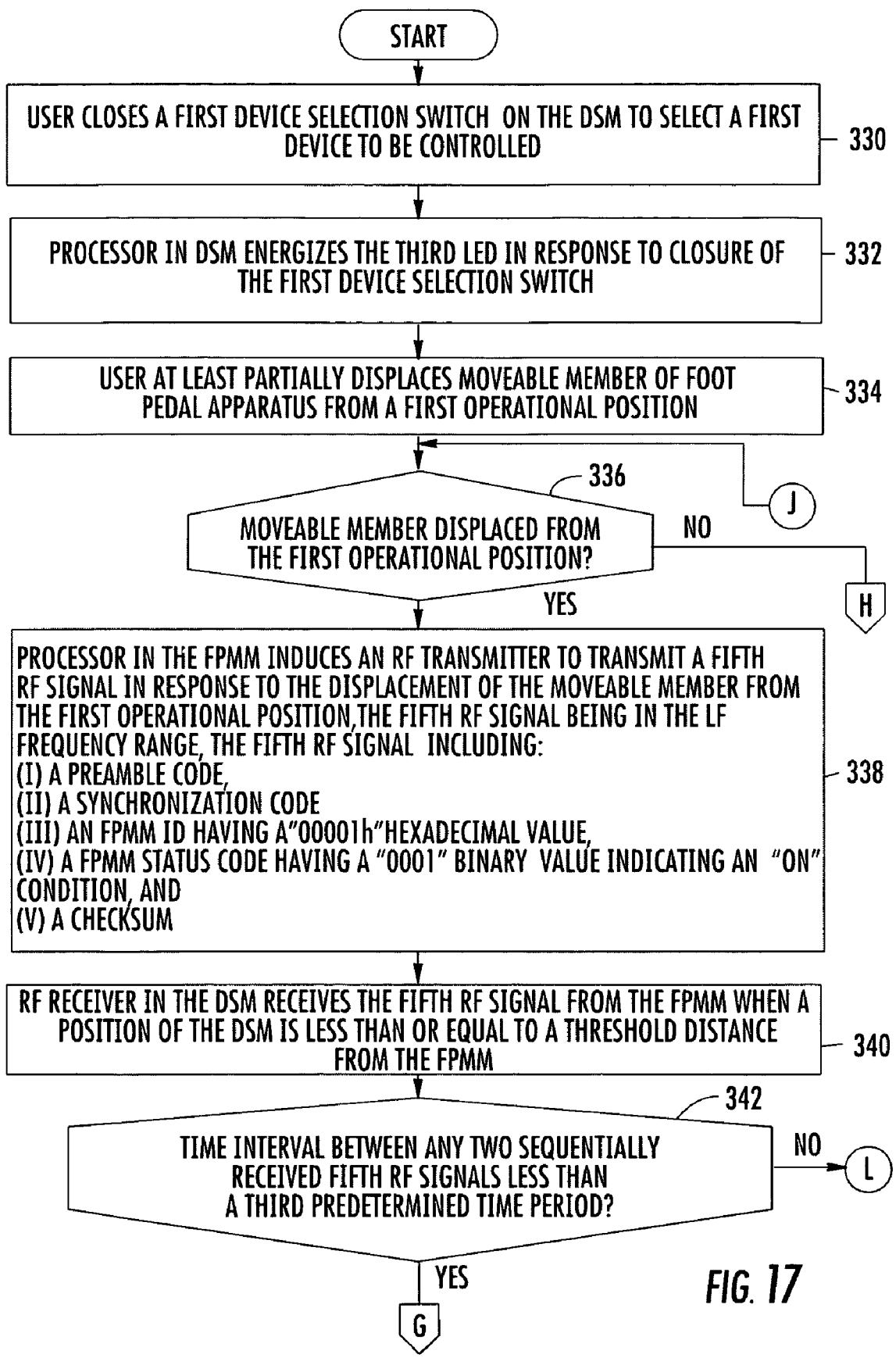
FIGS. 17-20 are flowcharts of a method for controlling the first device utilizing the system of FIG. 1.
Figure 18:
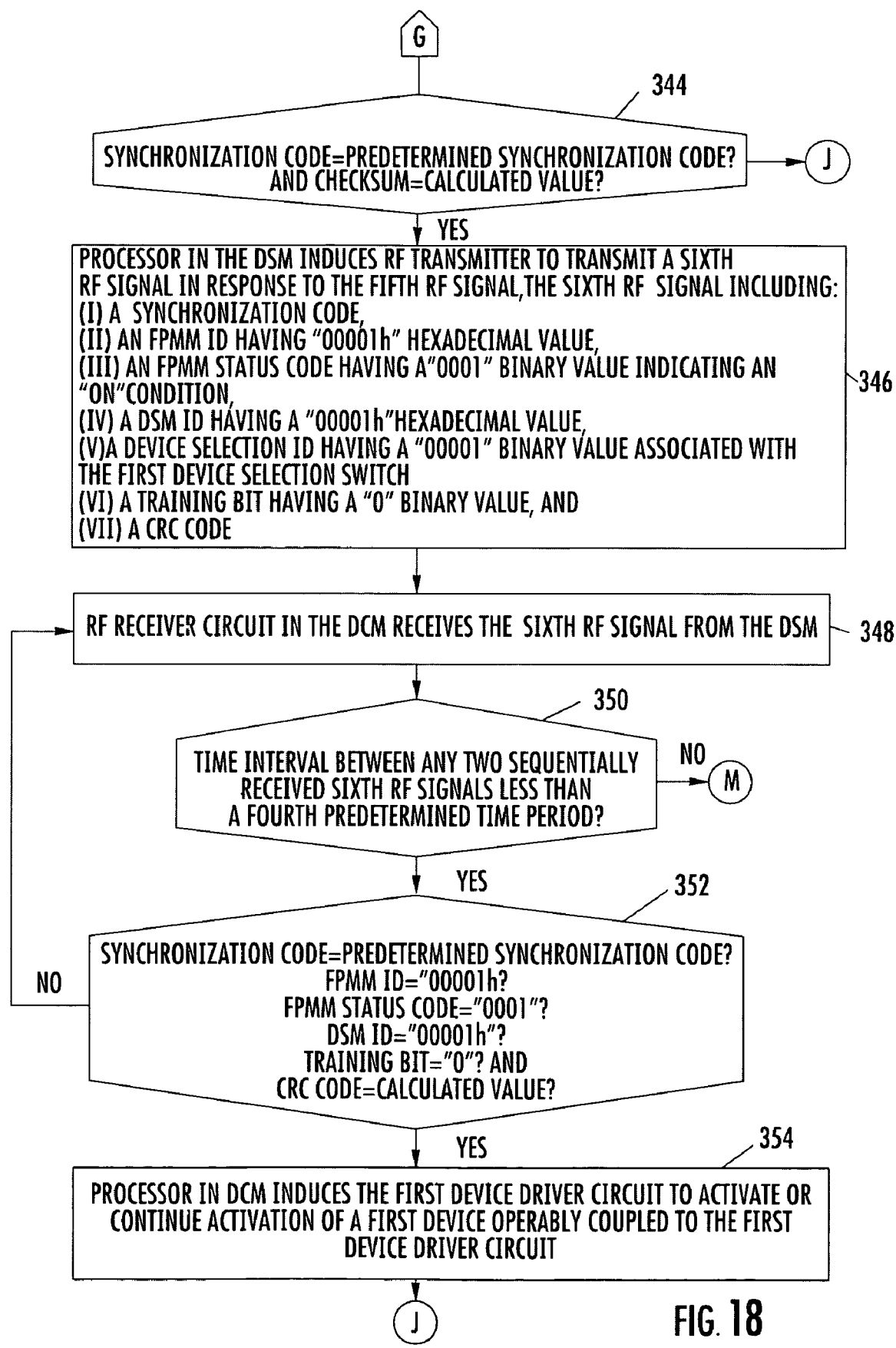
Figure 19:
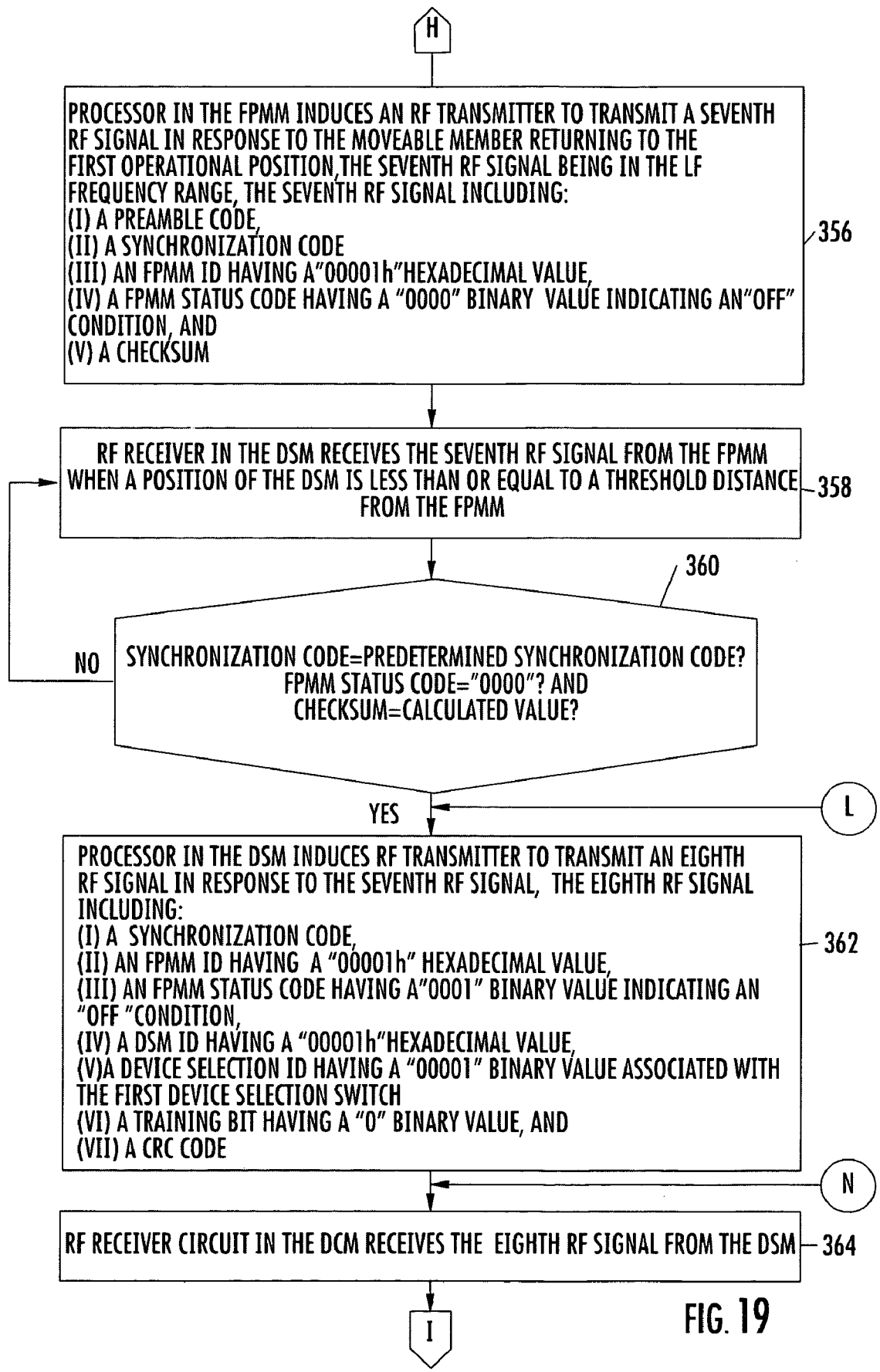
Figure 20:
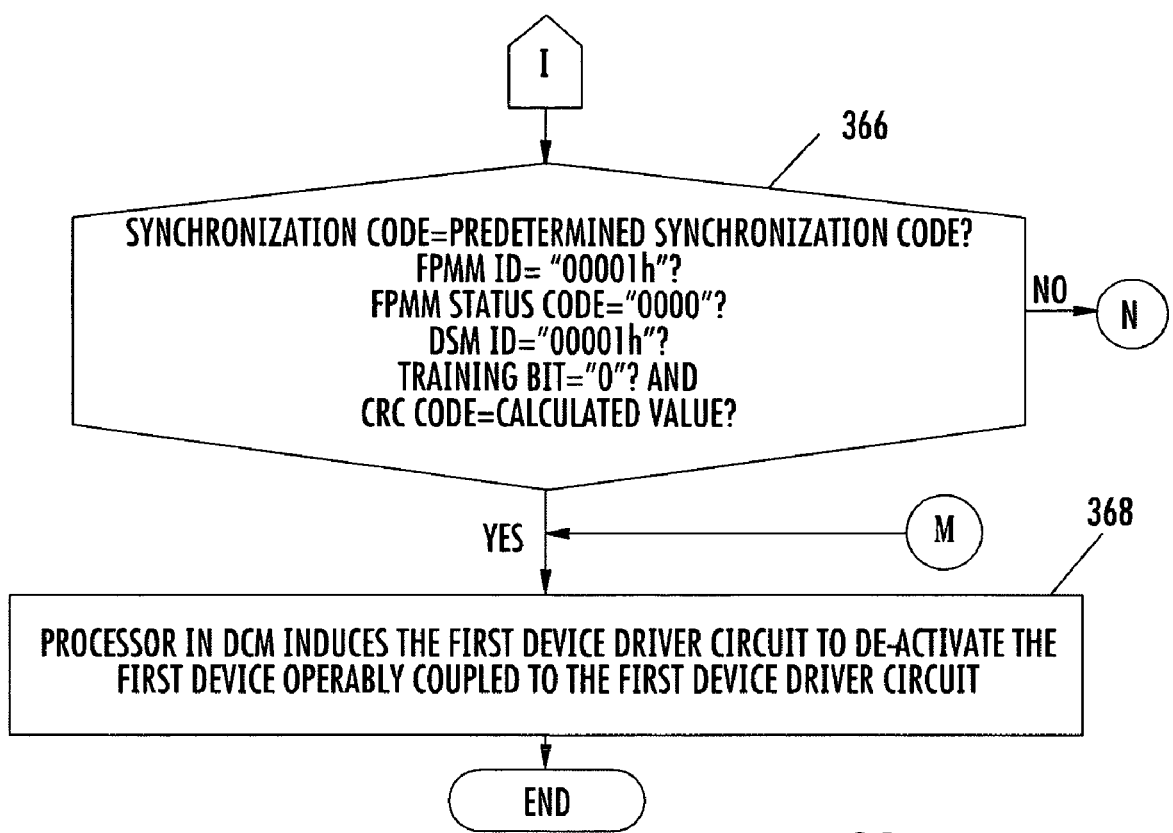
Figure 21:
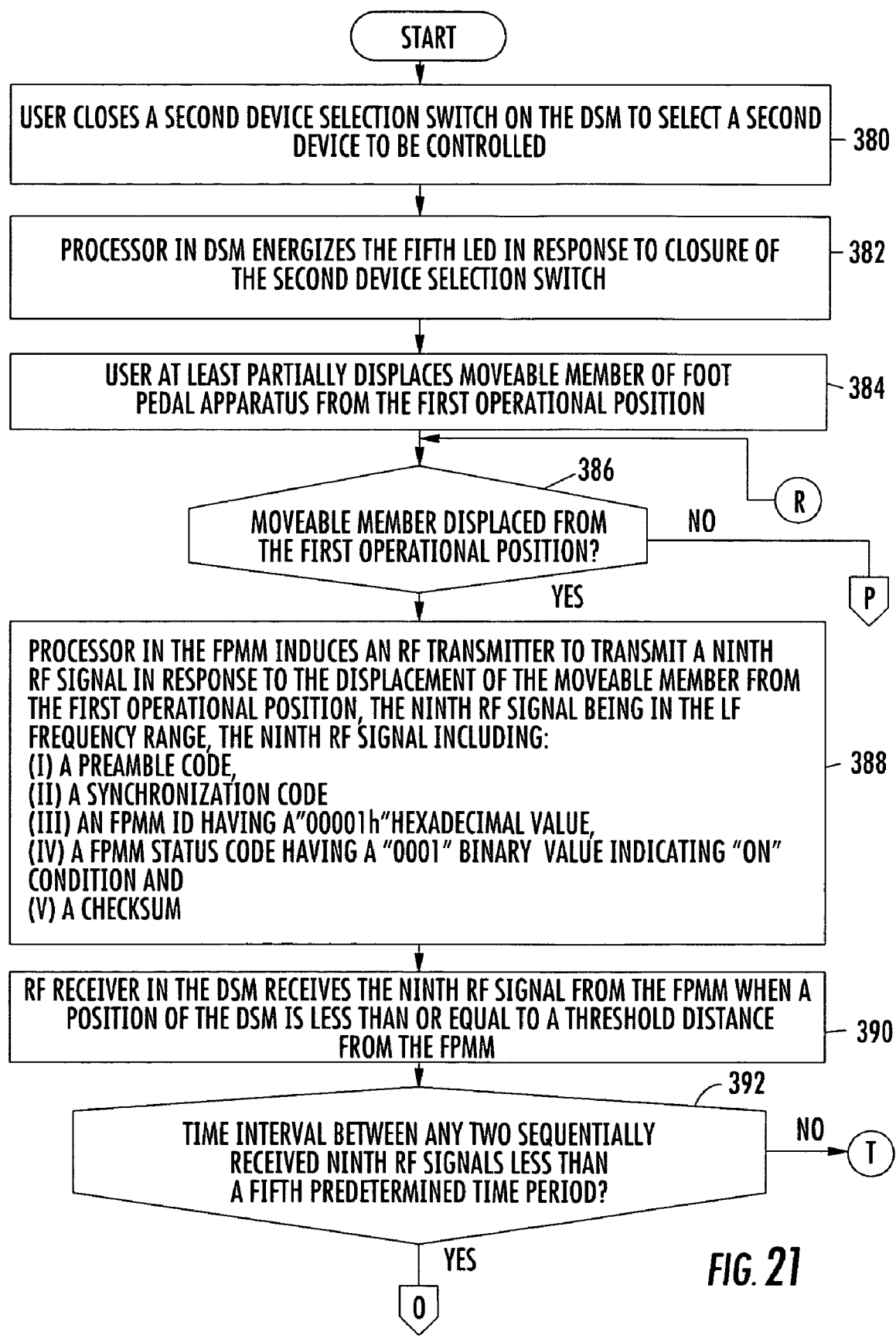
FIGS. 21-24 are flowcharts of the method for controlling the second device utilizing the system of FIG. 1.
Figure 22:
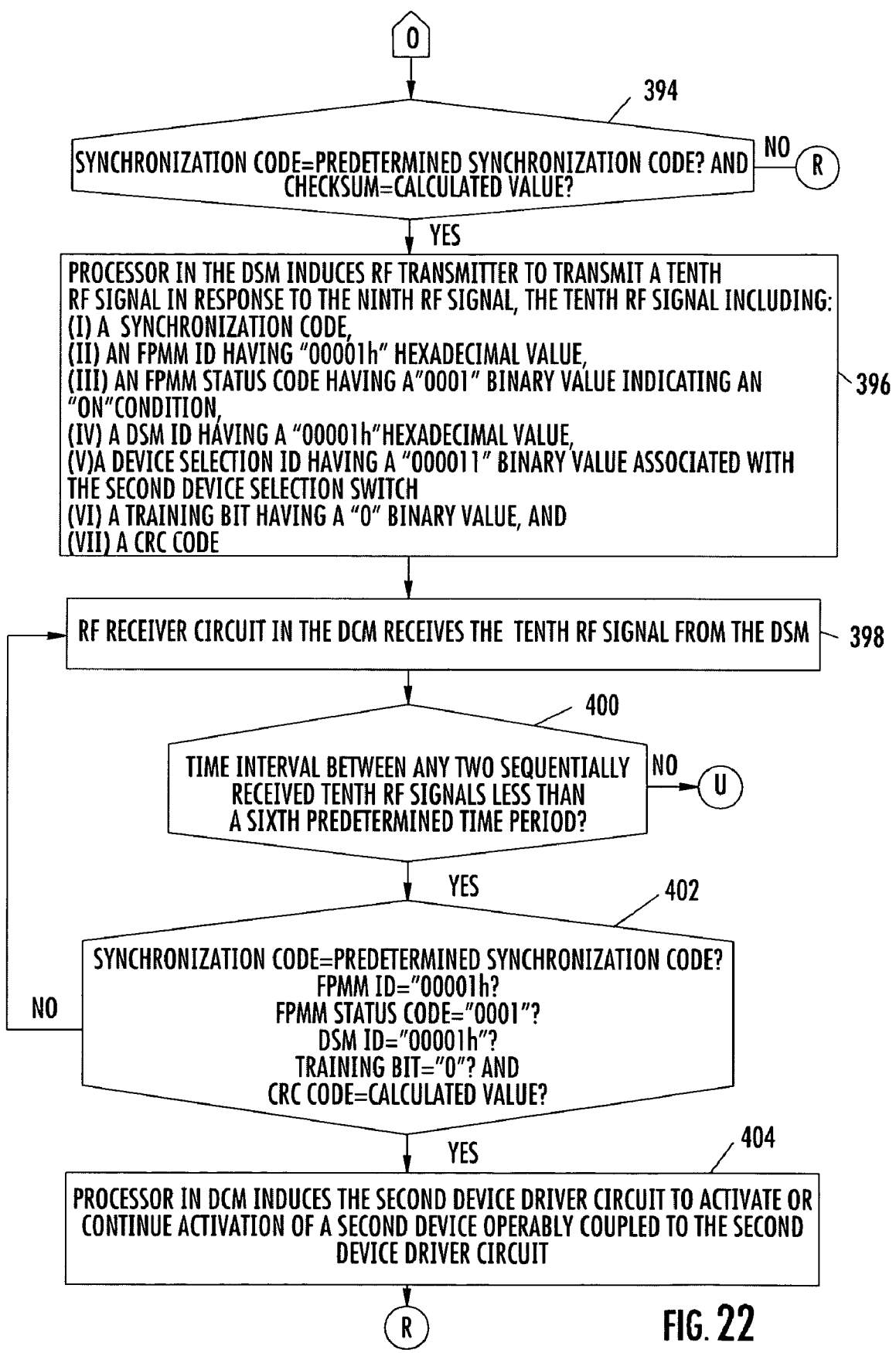
Figure 23:
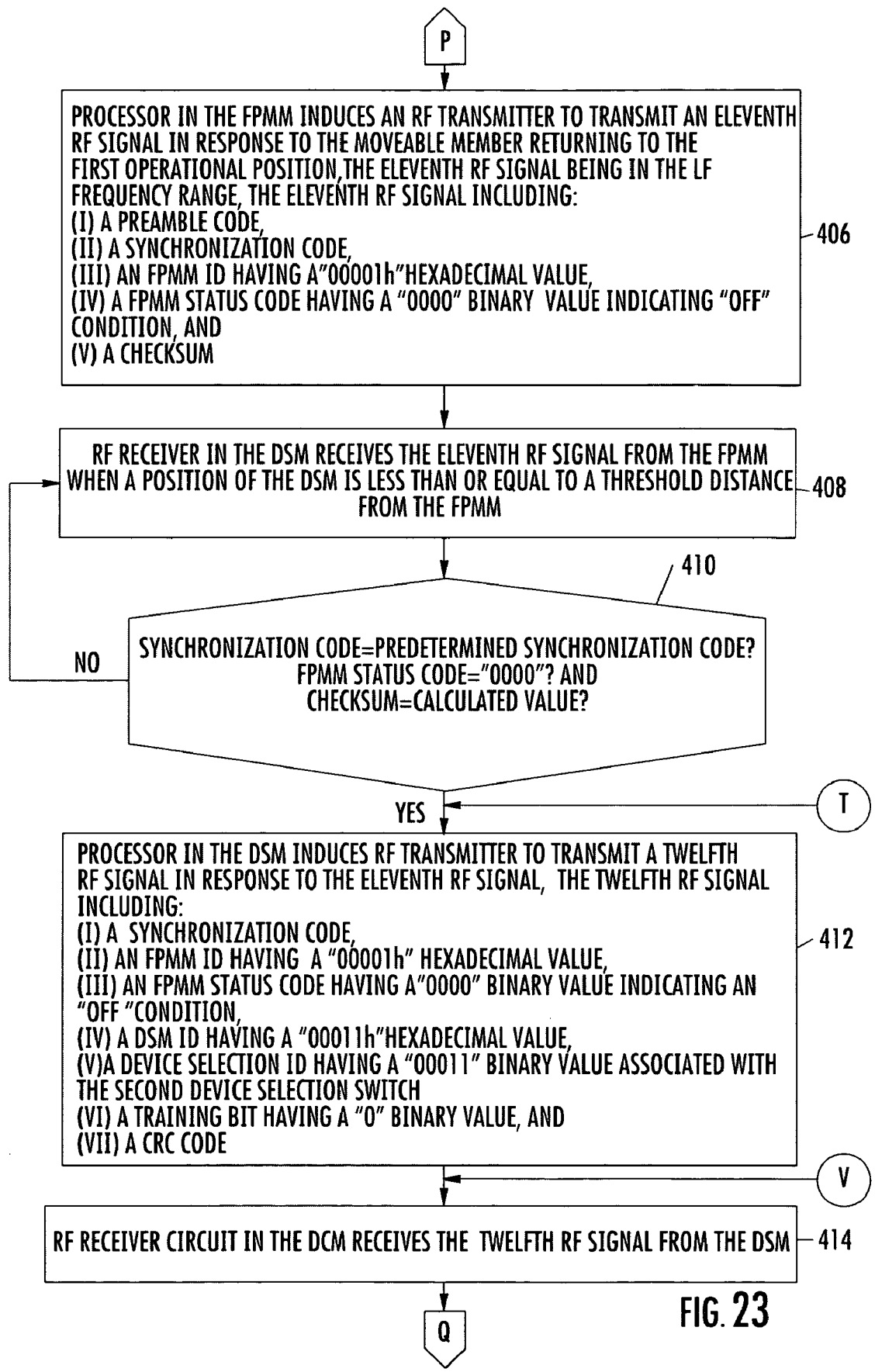
Figure 24:
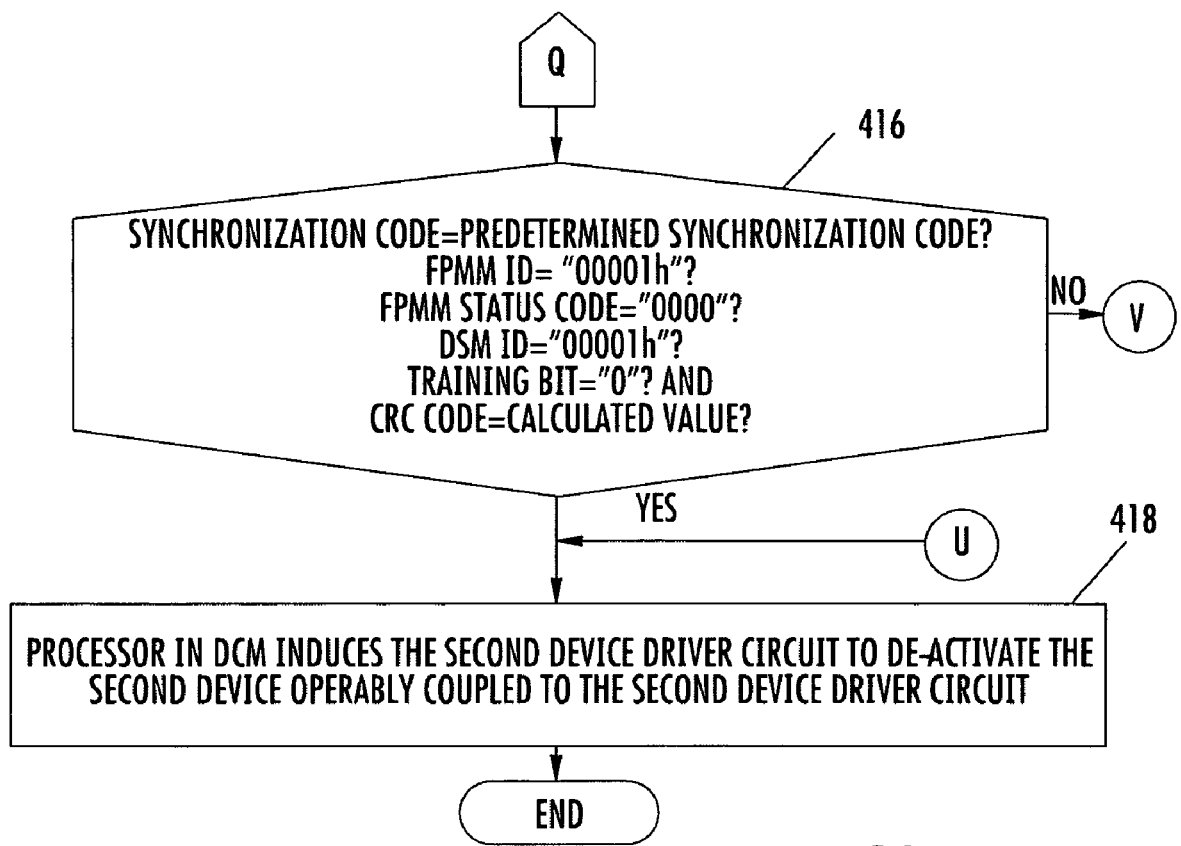

Referring to FIGS. 14-16, a method for training the DCM 16 to respond to RF signals from the DSM 14 for controlling the device 20 will now be explained. The method can be implemented utilizing the system 10 described above.

At step 280, the user closes a training mode switch 194 on the DCM 16, associated with an optically coupled bi-directional switch 212 therein, to induce the DCM 16 to enter the training operational mode.

Next at step 282, the processor 180 in the DCM 16 energizes an LED 198 in response to closure of the training mode switch 194 and resets and starts a third timer.

Next at step 284, the user closes the training mode switch 160 on the DSM 14 to induce the DSM 14 to enter a training operational mode.

Next at step 286, the processor 130 in the DSM 14 energizes the LED 166 in response to closure of the training mode switch 160.

Next at step 288, the user closes a device selection switch 158 on the DSM 14 to specify a second device selection ID having a "00011" binary value.

Next at step 290, the processor 130 in the DSM 14 energizes an LED 164 in response to closure of the device selection switch 158. The LED 164 is associated with the device selection switch 158. Further, the processor 130 resets and starts a fourth timer.

Next at step 292, the user at least partially displaces a moveable member 61 of the foot pedal apparatus 40 at from the first operational position.

Next at step 294, the processor 70 in the FPMM 42 generates a control signal to induce the RF transmitter 78 to iteratively transmit a third RF signal in response to the displacement of the moveable member 61 from the first operational position. In one embodiment, each third RF signal is in the LF frequency range. Further, each third RF signal includes: (i) a preamble code, (ii) a synchronization code, (iii) an FPMM ID having a "00001h" hexadecimal value, (iv) an FPMM status code having a "0001" binary value indicating an "on" condition, and (v) a checksum.

Next at step 296, the processor 130 makes a determination as to whether the fourth timer has a time value less than the second predetermined time value. If the value of step 296 equals "yes", the method advances to step 298. Otherwise, the method advances to step 314.

At step 298, the RF receiver 138 in the DSM 14 receives at least one of the third RF signals from the FPMM 42 when a position of the DSM 14 is less than or equal to a threshold distance from the FPMM 42.

Next at step 300, the processor 130 makes a determination as to whether the following conditions are present with respect to the third RF signal: (i) preamble code=predetermined preamble code, (ii) synchronization code=predetermined synchronization code, (iii) FPMM status code="0001", (iv) CRC code=calculated value. If the value of step 300 equals "yes", indicating the foregoing conditions are present, the method advances to step 302. Otherwise, the method returns to step 296.

At step 302, the processor 130 in the DSM 14 stores the FPMM ID from the third RF signal in the EEPROM 135.

Next at step 304, the processor 130 in the DSM 14 generates a control signal to induce the RF transmitter 152 to transmit a fourth RF signal in response to the third RF signal. In one embodiment each fourth RF signal includes: (i) a synchronization code, (ii) an FPMM ID having a "00001h" hexadecimal value, (iii) an FPMM status code having a "0001" binary value, (iv) a DSM ID having a "00001h" hexadecimal value, (v) a device selection ID having a "00011" binary value associated with the device selection switch 158 on the DSM 14, (vi) a training bit having a "1" binary value, and (vii) a CRC code.

Next at step 306, the processor 180 in the DCM 16 makes a determination as to whether the third timer has a time value less than the first predetermined time value. If the value of step 306 equals "yes", the method advances to step 308. Otherwise, the method advances to step 314.

At step 308, the RF receiver circuit 188 in the DCM 16 receives the fourth RF signal from the DSM 14.

Next at step 310, the processor 180 in the DCM 16 makes a determination as to whether the following conditions are present with respect to the fourth RF signal: (i) synchronization code=predetermined synchronization code, (ii) training bit="1" and (iii) CRC code=calculated value. If the value of step 310 equals "yes", the method advances to step 312. Otherwise, the method returns to step 306.

Next at step 312, the processor 180 in the DCM 16 stores in the EEPROM 185 a second record associated with the optically coupled bi-directional switch 212, including: (i) the FPMM ID having a "00001h" hexadecimal value, (ii) the DSM ID having a "00001h" hexadecimal value, and (iii) device selection ID having a "00011" binary value associated with the device selection switch 158 on the DSM 14.

Next at step 314, the processor 180 in the DCM 16 exits the training operational mode and de-energizes the LED 198.

Next at step 316, the user stops displacing the moveable member 61 of the foot pedal apparatus 40 from the first operational position, such that the moveable member 61 returns to the first operational position.

Next at step 318, the processor 130 in the DSM 14 exits the training operational mode and de-energizes the LEDs 164, 166. After step 318, the method is exited.

Referring to FIGS. 17-20, a method for controlling the device 18 utilizing the FPMM 42, the DSM 14, and the DCM 16 will now be explained.

At step 330, the user closes a device selection switch 156 on the DSM 14 to select the device 18 to be controlled.

Next at step 332, the processor 130 in the DSM 14 energizes the LED 162 in response to closure of the device selection switch 156.

Next at step 334, the user at least partially displaces moveable member 61 of foot pedal apparatus 40 from a first operational position.

Next at step 336, the processor 70 makes a determination as to whether the moveable member 61 is displaced from the first operational position. If the value of step 336 equals "yes", the method advances to step 338. Otherwise, the method advances to step 356.

At step 338, the processor 70 in the FPMM 42 generates a control signal to induce the RF transmitter 78 to transmit a fifth RF signal in response to the displacement of the moveable member 61 from the first operational position. In one embodiment, the fifth RF signal is in the LF frequency range. Further, the fifth RF signal includes: (i) a preamble code, (ii) a synchronization code, (iii) an FPMM ID having a "00001h" hexadecimal value, (iv) a FPMM status code having a "0001" binary value indicating an "on" condition, and (v) a checksum.

Next at step 340, the RF receiver 138 in the DSM 14 receives the fifth RF signal from the FPMM 42 when a position of the DSM 14 is less than or equal to a threshold distance from the FPMM 42. In one embodiment, the threshold distance is less than or equal to ten feet. Of course, in alternate embodiments, the threshold distance could be greater than ten feet.

Next at step 342, the processor 130 in the DSM 14 makes a determination as to whether a time interval between any two sequentially received fifth RF signals is less than a third predetermined time period. If the value of step 342 equals "yes", the method advances to step 344. Otherwise, the method advances to step 362.

At step 344, the processor 130 in the DSM 14 makes a determination as to whether the following conditions are present with respect to a fifth RF signal: (i) synchronization code=predetermined synchronization code, and (ii) checksum=calculated value. If the value of step 344 equals "yes", indicating the foregoing conditions are present, the method advances to step 346. Otherwise, the method returns to step 336.

At step 346, the processor 130 in the DSM 14 induces the RF transmitter 152 to transmit a sixth RF signal in response to the fifth RF signal. In one embodiment, the sixth RF signal includes: (i) a synchronization code, (ii) an FPMM ID having a "00001h" hexadecimal value, (iii) an FPMM status code having a "0001" binary value indicating an "on" condition, (iv) a DSM ID having a "00001h" hexadecimal value, (v) a device selection ID having a "00001" binary value associated with the device selection switch 156, (vi) a training bit having a "0" binary value, and (vii) a CRC code.

Next at step 348, the RF receiver circuit 188 in the DCM 16 receives the sixth RF signal from the DSM 14.

Next at step 350, the processor 180 in the DCM 16 makes a determination as to whether a time interval between any two sequentially received sixth RF signals is less than a fourth predetermined time period. If the value of step 350 equals "yes", the method advances to step 352. Otherwise, the method advances to step 368.

At step 352, the processor 180 in the DCM 16 makes a determination as to whether the following conditions are present with respect to the sixth RF signal: (i) synchronization code=predetermined synchronization code, (ii) FPMM ID="00001h", (iii) FPMM status code "0001", (iv) DSM ID="00001h", (v) training bit="0", (vi) CRC code=calculated value. If the value of step 352 equals "yes", indicating the foregoing conditions are present, the method advances to step 354. Otherwise, the method returns to step 348.

At step 354, the processor 180 in the DCM 16 generates a control signal to induce the optically coupled bi-directional switch 208 to activate or continue activation of the device 18 operably coupled to the optically coupled bi-directional switch 208. After step 354, the method returns to step 336.

Referring again to step 336, when a value of step 336 equals "no", indicating the movable member 61 is not displaced from the first operational position, the method advances to step 356.

At step 356, the processor 70 in the FPMM 42 generates a control signal to induce the RF transmitter 78 to transmit a seventh RF signal in response to the moveable member 61 returning to the first operational position. In one embodiment, the seventh RF signal is in the LF frequency range. Further, the seventh RF signal includes: (i) a preamble code, (ii) a synchronization code, (iii) an FPMM ID having a "00001h" hexadecimal value, (iv) an FPMM status code having a "0000" binary value indicating an "off" condition, and (v) a checksum.

Next at step 358, the RF receiver 138 in the DSM 14 receives the seventh RF signal from the FPMM 42 when a position of the DSM 14 is less than or equal to a threshold distance from the FPMM 42.

Next at step 360, the processor 130 in the DSM 14 makes a determination as to whether the following conditions are present with respect to the seventh RF signal: (i) synchronization code=predetermined synchronization code, (ii) FPMM status code="0000", and (iii) Checksum=calculated value. If the value of step 360 equals "yes", indicating the foregoing conditions are present, the method advances to step 362. Otherwise, the method returns to step 358.

At step 362, the processor 130 generates a control signal to induce the RF transmitter 152 to transmit an eighth RF signal in response to the seventh RF signal. In one embodiment, the eighth RF signal includes: (i) a synchronization code, (ii) an FPMM ID having a "00001h" hexadecimal value, (iii) an FPMM status code having a "0000" binary value indicating an "off" condition, (iv) a DSM ID having a "00001h" hexadecimal value, (v) a device selection ID having a "00001" binary value associated with the device selection switch 156, (vi) a training bit having a "0" binary value, and (vii) a CRC code.

Next at step 364, the RF receiver circuit 188 in the DCM 16 receives the eighth RF signal from the DSM 14.

Next at step 366, the processor 180 in DCM 16 makes a determination as to whether the following conditions are present in the eighth RF signal: (i) synchronization code=predetermined synchronization code, (ii) FPMM ID="00001h", (iii) FPMM status code="0000", (iv) DSM ID="00001h", (v) training bit="0" and (vi) CRC code=calculated value. If the value of step 366 equals "yes", indicating the foregoing conditions are present with respect to the eighth RF signal, the method advances to step 368. Otherwise, the method returns to step 364.

At step 368, the processor 180 in the DCM 16 induces the optically coupled bi-directional switch 208 to de-activate the device 18 operably coupled to the switch 208. After step 360, the method is exited.

Referring to FIGS. 21-24, a method for controlling the device 20 utilizing the FPMM 42, the DSM 14, and the DCM 16 will now be explained.

At step 380, the user closes the device selection switch 158 on the DSM 14 to select a device 20 to be controlled.

Next at step 382, the processor 130 in the DSM 14 energizes the LED 164 in response to closure of the device selection switch 158.

Next at step 384, the user at least partially displaces a moveable member 61 of foot pedal apparatus 40 from the first operational position.

Next at step 386, the processor 70 in the FPMM 12 makes a determination as to whether the movable member 61 is displaced from the first operational position. If the value of step 386 equals "yes", the method advances to step 388. Otherwise, the method advances to step 406.

At step 388, the processor 70 in the FPMM 42 induces the RF transmitter 78 to transmit a ninth RF signal in response to the displacement of the moveable member 61 from the first operational position. In one embodiment, the ninth RF signal is in the LF frequency range. Further, the ninth RF signal includes: (i) a preamble code, (ii) a synchronization code, (iii) an FPMM ID having a "00001h" hexadecimal value, (iv) a FPMM status code having a "0001" binary value indicating an "on" condition, and (v) a checksum.

Next at step 390, the RF receiver 138 in the DSM 14 receives the ninth RF signal from the FPMM 42 when a position of the DSM 14 is less than or equal to a threshold distance from the FPMM 42.

Next at step 392, the processor 130 in the DSM 14 makes a determination as to whether a time interval between any two sequentially received ninth RF signals is less than a fifth determined time period. If the value of step 392 equals "yes", the method advances to step 394. Otherwise, the method advances to step 412.

At step 394, the processor 130 in the DSM 14 makes a determination as to whether the following conditions are present with respect to the ninth RF signal: (i) synchronization code=predetermined synchronization code, and (ii) checksum=calculated value. If the value of step 394 equals "yes", indicating the foregoing conditions are present, the method advances to step 396. Otherwise, the method returns to step 386.

At step 396, the processor 130 in the DSM 14 generates a control signal to induce the RF transmitter 152 to transmit a tenth RF signal in response to the ninth RF signal. In one embodiment, the tenth RF signal includes: (i) a synchronization code, (ii) an FPMM ID having a "00001h" hexadecimal value, (iii) an FPMM status code having a "0001" binary value indicating an "on" condition, (iv) a DSM ID having a "00001h" hexadecimal value, (v) a device selection ID having a "00011" binary value associated with the device selection switch 158, (vi) a training bit having a "0" binary value, and (vii) a CRC code.

Next at step 398, the RF receiver circuit 188 in the DCM 16 receives the tenth RF signal from the DSM 14.

Next at step 400, the processor 180 in the DCM 16 makes a determination as to whether a time interval between any two sequentially received tenth RF signals is less than a sixth predetermined time period. If the value of step 400 equals "yes", the method advances to step 402. Otherwise, the method advances to step 418.

Next at step 402, the processor 180 in the DCM 16 makes a determination as to whether the following conditions are present with respect to the tenth RF signal: (i) synchronization code=predetermined synchronization code, (ii) FPMM ID="00001h", (iii) FPMM status code="0001", (iv) DSM ID="00001h", (v) training bit="0" and (vi) CRC code=calculated value. If the value of step 402 equals "yes", indicating the foregoing conditions are present, the method advances to step 404. Otherwise, the method returns to step 398.

At step 404, the processor 180 in the DCM 16 induces the optically coupled bi-directional switch 212 to activate or continue activation of a device 20 operably coupled to the optically coupled bi-directional switch 212. After step 404, the method returns to step 386.

Referring again to step to 386, when the value of step 386 equals "no", the method advances to step 406.

At step 406, the processor 70 in the FPMM 42 generate control signal to induce the RF transmitter 78 to transmit an eleventh RF signal in response to the moveable member 61 returning to the first operational position. In one embodiment, the eleventh RF signal is in the LF frequency range. Further, the eleventh RF signal includes: (i) a preamble, (ii) a synchronization code, (iii) an FPMM ID having a "00001h" hexadecimal value, (iv) an FPMM status code having a "0000" binary value indicating an "off" condition, and (v) a checksum.

Next at step 408, the RF receiver 138 in the DSM 14 receives the eleventh RF signal from the FPMM 42 when a position of the DSM 14 is less than or equal to a threshold distance from the FPMM 42.

Next at step 410, the processor 130 in the DSM 14 makes a determination as to whether the following conditions are present with respect to the eleventh RF signal: (i) synchronization code=predetermined synchronization code, (ii) FPMM status code="0000" and (iii) checksum=calculated value. If the value of step 410 equals "yes", the method advances to step 412. Otherwise, the method returns to step 408.

At step 412, the processor 130 in the DSM 14 generates a control signal to induce the RF transmitter 152 to transmit a twelfth RF signal in response to the eleventh RF signal. In one embodiment, the twelfth RF signal includes: (i) a synchronization code, (ii) an FPMM ID having a "00001h" hexadecimal value, (iii) an FPMM status code having a "0000" binary value indicating an "off" condition, (iv) a DSM ID having a "00011h" hexadecimal value, (v) a device selection ID having a "00011" binary value associated with the device selection switch 158, (vi) a training bit having a "0" binary value, and (vii) a CRC code.

Next at step 414, the RF receiver circuit 188 in the DCM 16 receives the twelfth RF signal from the DSM 14.

Next at step 416, the processor 180 in the DCM 16 makes a determination as to whether the following conditions are present with respect to the twelfth RF signal: (i) synchronization code=predetermined synchronization code, (ii) FPMM ID="00001h", (iii) FPMM status code="0000", (iv) DSM ID="00001h", (v) training bit="0", and (vi) CRC code=calculated value. If the value of step 416 equals "yes", indicating a foregoing conditions are present, the method advances step 418. Otherwise, the method returns to step 414.

At step 418, the processor 180 in the DCM 16 induces the optically coupled bi-directional switch 212 to de-activate the device 20 operably coupled to the switch 212. After step 418, the method is exited.

The inventive system and method for remotely controlling devices provide a substantial advantage over other systems and methods. In particular, the system and method provide a technical effect of controlling devices using first, second, and third RF modules, where the third wireless RF module only responds to RF signals having first and second identifiers associated with the first and second modules, respectively, for controlling the devices. As a result, inadvertent activation of the devices by the third module due to extraneous RF signals is prevented.

While the invention is described with reference to the exemplary embodiments, it will be understood by those skilled in the art that various changes may be made an equivalence may be substituted for elements thereof without departing from the scope of the invention. In addition, many modifications may be made to the teachings of the invention to adapt to a particular situation without departing from the scope thereof. Therefore, is intended that the invention not be limited the embodiments disclosed for carrying out this invention, but that the invention includes all embodiments falling with the scope of the intended claims. For purposes of claim interpretation, the term "module" is defined as any device, component, or group of components, that can perform at least one task or operation. The use of the term's first, second, etc. does not denote any order of importance, but rather the term's first, second, etc. are to distinguish one element from another.

What is claimed is:

1. A system for remotely controlling at least a first device based on operation of a foot pedal apparatus, the foot pedal apparatus having a movable member, comprising:
 a first module configured to transmit a first RF signal in response to at least partial displacement of the moveable member of the foot pedal apparatus from a first operational position, the first signal having a first binary identifier associated with the first module, and a first activation binary command;
 a second module configured to receive the first RF signal and to transmit a second RF signal having the first binary identifier, the first activation binary command, and a second binary identifier associated with the second module, in response to the first RF signal;
 a third module configured to receive the second RF signal; the third module further configured to compare the first and second binary identifiers in the second RF signal with first and second binary values, respectively, stored in a memory device of the third module;
 the third module further configured to compare the first activation binary command with a first binary command value stored in the memory device; and
 the third module further configured to activate the first device when the first and second binary identifiers correspond to the first and second binary values, respectively, and the first activation binary command corresponds to the first binary command value.

2. The system of claim 1, wherein the first module is further configured to detect at least partial displacement of the moveable member of the foot pedal apparatus by monitoring a pressure level in a conduit operably coupled to the foot pedal apparatus.

3. The system of claim 1, wherein the first module is further configured to detect at least partial displacement of the moveable member of the foot pedal apparatus by monitoring a displacement signal indicative of displacement of the moveable member.

4. The system of claim 1, wherein the first module is further configured to transmit a third RF signal having the first binary identifier and a de-activation binary command after transmitting the first RF signal when the moveable member is substantially at the first operational position;
 the second module further configured to transmit a fourth RF signal having the first and second binary identifiers and the de-activation binary command in response to receiving the third RF signal;
 the third module further configured to receive the fourth RF signal and to compare the first and second binary identifiers in the fourth RF signal with the first and second binary values, respectively, stored in the memory device of the third module;
 the third module further configured to compare the de-activation binary command with a second binary command value stored in the memory device; and
 the third module further configured to de-activate the first device when the first and second binary identifiers in the fourth RF signal correspond to the first and second binary values, respectively, and the de-activation binary command corresponds to the second binary command value.

5. The system of claim 1, wherein the first module is further configured to transmit a third RF signal having the first binary identifier after transmitting the first RF signal when the moveable member remains displaced from the first operational position;
 the second module further configured to transmit a fourth RF signal having the first and second binary identifiers and the first activation binary command in response to receiving the third RF signal;
 the third module further configured to receive the fourth RF signal and to compare the first and second binary identifiers in the fourth RF signal with the first and second binary values, respectively, stored in the memory device of the third module;
 the third module further configured to compare the first activation binary command in the fourth RF signal with the first binary command value stored in the memory device; and
 the third module is further configured to maintain activation of the first device during a first time period from at least receipt of the second RF signal to receipt of the fourth RF signal, if the first time period is less than or equal to a threshold time period and the first and second binary identifiers in the fourth RF signal correspond to the first and second binary values, respectively, and the first activation binary command in the fourth RF signal corresponds to the first binary command value.

6. The system of claim 5, wherein the third module is configured to de-activate the first device if the first time period is greater than a threshold time period.

7. The system of claim 1, wherein the first RF signal is transmitted at a frequency less than or equal to 160 kilohertz.

8. The system of claim 1, wherein the second RF signal is transmitted at a frequency within a frequency band of 260-470 megahertz.

9. The system of claim 1, wherein the first device comprises a dental implement or a medical implement.

10. The system of claim 1, wherein the first device comprises one of a drill, a microprocessor position-controllable dental chair, an infrared photo-optic imaging camera, a dental irrigator, an intra-oral camera, a video capture circuit, a laser, an air-abrasion unit, an electro-surgery unit, an ultrasonic teeth cleaning unit, a piezo-ultrasonic unit, an air polishing prophylaxis device, a gum depth measurement probe, a surgical microscope with controllable focusing adjustment, a microprocessor controlled anesthetic delivery system, and an endodontic heat source device.

11. The system of claim 1, wherein the first device comprises a video capture circuit, the third module operably coupled to the video capture circuit, the third module configured to receive the second RF signal and to induce the video capture circuit to store a video image in a memory in response to the second RF signal.

12. A method for remotely controlling at least a first device based on operation of a foot pedal apparatus having a movable member, comprising:
transmitting a first RF signal from a first module in response to at least partial displacement of the moveable member of the foot pedal apparatus from a first operational position, the first RF signal having a first binary identifier associated with the first module, and a first activation binary command;
transmitting a second RF signal from a second module having the first binary identifier, the first activation binary command, and a second binary identifier associated with the second module, in response to the first RF signal;
receiving the second RF signal at a third module;
comparing the first and second binary identifiers in the second RF signal with first and second binary values, respectively, stored in a memory device of the third module, utilizing the third module;
comparing the first activation binary command with a first binary command value stored in the memory device, utilizing the third module; and
activating the first device when the first and second binary identifiers correspond to the first and second binary values, respectively, and the first activation binary command corresponds to the first binary command value, utilizing the third module.

13. The method of claim 12, further comprising:
transmitting a third RF signal from the first module having the first binary identifier and a de-activation binary command after transmitting the first RF signal when the moveable member is substantially at the first operational position;
transmitting a fourth RF signal from the second module having the first and second binary identifiers and the de-activation binary command in response to receiving the third RF signal;
receiving the fourth RF signal at the third module;
comparing the first and second binary identifiers in the fourth RF signal with the first and second binary values, respectively, stored in the memory device of the third module, utilizing the third module;
comparing the de-activation binary command with a second binary command value stored in the memory device, utilizing the third module; and
de-activating the first device when the first and second binary identifiers in the fourth RF signal correspond to the first and second binary values, respectively, and the de-activation binary command corresponds to the second binary command value, utilizing the third module.

14. The method of claim 12, further comprising:
transmitting a third RF signal from the first module having the first binary identifier after transmitting the first RF signal when the moveable member remains displaced from the first operational position;
transmitting a fourth RF signal from the second module having the first and second binary identifiers and the first binary activation binary command in response to receiving the third RF signal;
receiving the fourth RF signal at the third module;
comparing the first and second binary identifiers in the fourth RF signal with the first and second binary values, respectively, stored in the memory device of the third module, utilizing the third module;
comparing the first activation binary command in the fourth RF signal with the first binary command value, utilizing the third module; and
maintaining activation of the first device utilizing the third module during a first time period from at least receipt of the second RF signal to receipt of the fourth RF signal, if the first time period is less than or equal to a threshold time period, and the first and second binary identifiers in the fourth RF signal correspond to the first and second binary values, respectively, and the first activation binary command in the fourth RF signal corresponds to the first binary command value.

* * * * *